United States Patent [19]
Almen et al.

[11] Patent Number: 5,482,699
[45] Date of Patent: * Jan. 9, 1996

[54] MULTINUCLEAR COMPLEXES FOR X-RAY IMAGING

[75] Inventors: Torsten Almen, Malmö, Sweden; Arne Berg, Blommenholm, Norway; C. Allen Chang, Palo Alto; Michael Droege, Livermore, both of Calif.; Harald Dugstad, Oslo, Norway; Jere D. Fellman, Livermore; Sook-Hui Kim, Mountain View, both of Calif.; Jo Klaveness, Oslo, Norway; Scott M. Rocklage, Los Gatos, Calif.; Pål Rongved, Hellvik, Norway; Brent Segal, Sunnyvale; Alan D. Watson, Campbell, both of Calif.

[73] Assignee: Nycomed Salutar Inc., Sunnyvale, Calif.

[ * ] Notice: The portion of the term of this patent subsequent to Oct. 17, 2012, has been disclaimed.

[21] Appl. No.: 122,461

[22] PCT Filed: Mar. 27, 1992

[86] PCT No.: PCT/EP92/00698

§ 371 Date: Sep. 24, 1993

§ 102(e) Date: Nov. 24, 1993

[87] PCT Pub. No.: WO92/17215

PCT Pub. Date: Oct. 15, 1992

[30] Foreign Application Priority Data

Mar. 27, 1991 [GB] United Kingdom .................. 9106579
Sep. 26, 1991 [GB] United Kingdom .................. 9120507

[51] Int. Cl.$^6$ .................................................. A61K 49/04
[52] U.S. Cl. ........................... 424/9.42; 534/15; 534/16; 556/8; 556/31; 556/61; 540/474; 514/836
[58] Field of Search ...................... 4247/4, 9.42; 534/15, 534/16; 556/8, 31, 61; 540/474; 514/836

[56] References Cited

U.S. PATENT DOCUMENTS

| 3,763,188 | 10/1973 | Krespan | 260/338 |
| 3,860,611 | 1/1975 | Krespan | 260/338 |
| 3,952,015 | 4/1976 | Krespan | 260/338 |
| 4,079,124 | 3/1978 | Winchell | 424/4 |
| 4,176,173 | 11/1979 | Winchell et al. | 424/5 |
| 4,647,447 | 3/1987 | Gries et al. | 424/9 |
| 4,826,673 | 5/1989 | Dean et al. | 424/9 |

FOREIGN PATENT DOCUMENTS

| 0130934 | 6/1984 | European Pat. Off. . |
| 0263059 | 9/1987 | European Pat. Off. . |
| 0361960 | 9/1989 | European Pat. Off. . |
| 2348699 | 11/1977 | France . |
| 8602352 | 4/1986 | WIPO . |
| 8900557 | 1/1989 | WIPO . |
| 8910372 | 11/1989 | WIPO . |
| 9003190 | 4/1990 | WIPO . |
| 9003190 | 5/1990 | WIPO . |
| 9115467 | 10/1991 | WIPO . |
| 9114460 | 10/1991 | WIPO . |
| 9217214 | 10/1992 | WIPO . |

OTHER PUBLICATIONS

Novak et al., Tungsten (V) Complexes of Ethylenediaminetetraacetic Acid. med. Chem. 1974, vol. 36, pp. 1061–1065.
Saito et al., Synthesis of . . . for Superconducting Chevrel Phases, J. Am. Chem. Soc., 1988, 110, 1646–1647.
Shibahara et al., Preparation of Triangular (IV) Aqua Ion, . . . , J. Am. Chem. Soc., 1986, 108, 2757–2758.
Ott et al., Di–µ–oxo, µ–Oxo–sulfido, and . . . , Inorganic Chemistry, vol. 16, No. 10, 1977, pp. 2538–2545.
Shibahara et al., Cubane–Type Mixed–Metal Clusters with . . . , Inorg. Chem. 1991, 30, 2693–2699.
Dedeian et al., Sulfur–Bridged Incomplete Cubane–Type . . . , Inorg. Chem. 1991, 30, 1687, 1688.
Nakata et al., Kinetic Studies on the Terminal–Ligand–Substition . . . , Inorg. Chem. 1991, 30, 1575–1579.
Kim et al., The Cubane Structure of . . . , Inorg. Chem. 1991, 30, 574, 577.
Dimmock et al., Solution Studies on the Cuboidal Mixed–Metal Complex . . . , Inorg. Chem. 1990, 29, 5120–5125.
Saito et al., Synthesis, Structure, and Electronic Properties of . . . , Inorg. Chem., 1989, 28, 3588–3592.
Richens et al., Crystal Structure of and Mechanism of . . . , Inorg. Chem., 1989, 28, 1394–1402.
Cotton et al., Synthesis and Structural Characterization of . . . , Inorg. Chem., 1989, 28, 2623–2630.
Ikari et al., A New Mixed Molybdenum–Tungsten . . . , Inorg. Chem., 1989, 28, 1248–1254.
Ikari et al., (µ–Ethylenediaminetetraacetato) . . . , Inorg. Chem., 1989, 28, 447–451.
Cotton et al., Derivatization of the Cuboidal . . . , Inorg. Chem., 1986, 3529–3532.
Hogue et al., Chemistry of Polynuclear Metal Halides . . . , Inorganic Chem., vol. 9, No. 6, Jun. 1970, pp. 1354–1360.
Newton et al., Synthesis and Molecular Structure of . . . , Inorganic Chemistry, vol. 18, No. 6, 1979, pp. 1621–1626.
Blackmer et al., Conformational Dynamics of Dioxodi–µ–oxo– . . . , Inorganic Chemistry, vol. 15, No. 3, 1976, pp. 596–601.
Schrock et al., Preparation of W . . . , Inorg. Chem. 1983, 22, pp. 2801–2806.

(List continued on next page.)

*Primary Examiner*—Gary E. Hollinden
*Attorney, Agent, or Firm*—Fish & Richardson

[57] ABSTRACT

An imaging contrast medium comprising a physiologically tolerable multinuclear complex (as defined in claim 1) is disclosed. The multinuclear complex contains at least two, but preferably three or more contrast enhancing atoms. For X-ray or ultrasound imaging techniques heavy metal atoms are used to enhance contrast, whereas in Magnetic Resonance Imaging paramagnetic metal atoms are contrast enhancing. Molybdenum and tungsten are preferred contrast enhancing atoms. The medium may also be used therapeutically.

27 Claims, No Drawings

OTHER PUBLICATIONS

Kathirgamanathan et al., Effect of Equivalent and Nonequivalent Site . . . , Inorg. Chem. 1985, 24, 2950–2954.

Ooi et al., Substitution and Redox Properties . . . , Inorg. Chem. 1988, 27. 3626–3629.

Pan et al., Reactions of Tetrathiometales, MS . . . , Inorg. Chem., 1984, 23, 4265–4269.

Shibahara et al., Double–Cubane–Type Molybdenum–Sulfur . . . , J. Am. Chem. Soc., 1987, 109, 3495–3496.

Cotton et al., The $Mo^3S^{4+}_4$ Aquo Ion, J. Am. Chem. Soc., 1985, 107, pp. 6734–6735.

Halbert et al., Synthesis, Structure, and Reactivity of . . . , J. Am. Chem. Soc., 1984, 106, 1849–1851.

Shibahara et al., A Novel Cubane–Type . . . , J. Am. Chem. Soc., 1984, 106, 789–791.

Weigel et al., Isonitrile Binding to a Site–Differentiated . . . , J. Am. Chem. Soc., 1990, 112, 8015–8023.

Hagen et al., Synthetic Routes to . . . , J. Am. Chem. Soc., 1983, 105, 3905–3913.

Martinez et al., Reaction Paths in the Formation of Triangular . . ., J. Am. Chem. Soc., 1987, 109, 4615–4619.

Stack et al., Subsite–Differentiated Analogues of . . . , J. Am. Chem. Soc., 1988, 110, 2484–2494.

Shibahara et al., Structures and Properties of Cubane–type . . . , Inorganica Chimica Acta., 116 (1986) L25–L27.

Shibahara et al., Preparation of Tungsten (V) Aqua Ion . . . , Chemistry Letters, pp. 2327–2330, 1987.

Lee et al., Nonmolecular Metal Chalcogenide/halide Solids . . . Angew. Chem. Int. Ed. Engl. 29 (1990) 840–856.

Berry et al., Synthesis of Metal Molybdenum Tellurides . . . , J. Am. Chem. Soc. Dalton Trans. 1991, pp. 57–59.

Drew et al., Dimeric Tungsten (V) Compounds containing . . . , J. Am. Chem. Soc. Dalton Trans. 1987, pp. 1163–1167.

Wharton et al., Mechanism of the Oxidation of the Molybdenum . . . , J. C. S. Dalton, 1975, pp. 1526–1530.

Henkel et al., Preparation, Structure, and properties of the Mo/Se Ions . . . , J. Chem. Soc., Chem. Commun., 1990, pp. 1014–1016.

Kathirgamanathan et al., Complete Synthesis of the Series of Triangular Oxo/Sulphido . . ., J. Chem. Soc. Commun., 1985, pp. 1437–1439.

Ooi et al., Solution Properties and Reactivity of the Aqua Ion of the . . . , Inorganic Chemistry 1989, 28, 3799–3804.

Bino et al., A Trinuclear Molybdenum (IV) Cluster Compound . . . , J. Am. Chemcial Society, 100, Aug. 2, 1978, pp. 5252–5253.

Hollingshead et al., A Novel Oxyen–Centered Hexanuclear Molybdenum Alkoxide Cluster, . . . , J. Am. Chem. Soc. 1990 112, pp. 7402–7403.

Wasfi et al., Protonation–Induced Dynamic Stereochemistry of Hexafungstobis (organoarsonate) Anions, J. Am. Chem. Soc., 1978, 100, pp. 7786–7787.

Bunzey et al., Molybdenum Complexes of Aliphatic Thiols. Isolation and Characterization of Two Isomeric Forms . . ., J. Am. Chem. Socl., 1977, 99:12, pp. 4168–4170.

Febin et al., Triangular Thiocomplexes of Molydbdenum: Reactions with Halogens, Hydrochalogen Acids and Phosphines, Inorganic Chimica Acta, 167 (1990) pp. 39–45.

Hegetschweiler et al., A New Synthetic Pathway for . . . , Inorganica Chimica Acta, 169 (1990) pp. 235–243.

Shibahara et al., Preparation of Incomplete Cubane–type . . . , Inorganica Chimica Acta, 113 (1986) L19–L21.

Cotton et al., A New Reaction Converting the . . . , Inorganica Chimica Acta, 102 (1985) L25–L27.

Müller et al., Activation and Sulfur–Atom Transfer Reaction of Cluster–Bonded . . . , Angew, Chem. Int. Ed. Engl. 19 (1980) No. 1, pp. 72–73.

Müller et al., A Cluster with High Negative Charge and Cubane–. . . , Angew. Chem. Int. Ed. Engl. 21 (1982) No. 10, pp. 795–796.

Krespan, Functionalized Macroheterobicycle Compounds, The Journal of Organic Chem., vol. 45, No. 7, pp. 1177–1180, Mar. 28, 1980.

Krespan, The Oxetane Function Sprio to Polyoxaaza Macroheterocycles, J. Org. Chem. vol. 40, No. 9, 1975, pp. 1205–1209.

Krespan, Macroheterocycles, The Oxetane Function Spiro to Macrocyclic Polyether Rings, J. Org. Chem. vol. 39, No. 16, 1974, pp. 2351–2355.

Campbell, Some Reactions of 3,3–Bis(chloromethyl)oxetane, Journal Organic Chemistry, Sep. 1957, vol. 202, pp. 1029–1035.

Tomohiro et al., Macrocyclic Tetranuclear Clusters with 28–, 32–, 36–, 40–, and 44–Membered Rings as High . . . , J. Chem. Soc. Dalton Trans., 1990, pp. 2459–2463.

Nasreldin et al., Kinetics of 1:1 NCS–for . . . , J. Chem. Soc. Dalton Trans., 1990, pp. 1765–1769.

Dimmock et al., Mechanism of the Reaction of Cuboidal . . . , J. Chem. Soc. Dalton Trans., 1990, pp. 3101–3106.

Shibahara et al., Preparation and Characterization of Dimeric Molybdenum (III)–Ethylene–diaminetetra–acetate Complexes, J. Chem. Soc., Dalton Trans. 1978, pp. 95–99.

Kathirgamanathan et al., A Novel Electrochemical Method for the Preparation of Triangular and Cubic . . ., J. Chem. Soc. Chem. Commun., 1985, pp. 953–954.

Bandy et al., Synthesis, Crystal Structures, and Bonding of the Molybdenum Cubane . . . , J. Chem. Soc. Chem. Commun., 1983, pp. 1395–1397.

Müller et al., Disulfur Compleses, Coordination Chemistry Reviews, 46, 1982 pp. 245–280.

Tsigdinos, Heteropoly Compounds of Molybdenum and Tungsten . . . , Molybdenum Chemicals Chemical Data Series Bulletin Cdb–12a (Nov. 1969) pp. 1–24.

Müller et al., Crystal Structure of . . . , Z. Naturforsch, 34B, pp. 434–436 (1979).

Shibahara et al., Preparation of Trinuclear Molybdenum (IV) Ion, . . . , Polyhedron, 5:357–361 (1986).

Day et al., Metal Oxide Chemistry in Solution: The Early Transition Metal Polyoxoanions, Science. vol. 228, No. 4699, May 3, 1985, pp. 533–541.

Fedorov et al., New Methods of Synthesising the Cluster Molybdenum Sulphide Halides . . ., Russian Journal of Inorganic Chemistry, 31 (10), 1986, pp. 1429–1431.

Barbaro et al., The Tetranuclear Trianion . . . , J. Am. Chem. Soc., 1990, 112, pp. 7238–7246.

Siedle et al., Aryl–Substituted Molecular Metal Oxide Clusters, J. Am. Chem. Soc., 1986, 108, pp. 6430–6431.

MULTINUCLEAR COMPLEXES FOR X-RAY IMAGING

This application is a 371 of PCT/EP92/00698 filed Mar. 27, 1992.

The present invention relates to the use in diagnostic imaging, in particular X-ray, ultrasound and scintigraphy of contrast agents comprising complexes of multinuclear moieties, and to contrast media containing such complexes.

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedure, i.e. increased contrast can lead to increased spatial resolution.

The diagnostic quality of images is strongly dependent on the inherent noise level in the imaging procedure - and the ratio of the contrast level to the noise level can thus be seen to represent an effective diagnostic quality factor for diagnostic images.

Achieving improvement in such a diagnostic quality factor has long been and still remains an important goal. In techniques such as X-ray and ultrasound, one approach to improving the diagnostic quality factor has been to introduce contrast enhancing materials, contrast agents, into the body region being imaged.

Thus in X-ray for example early examples of contrast agents were insoluble inorganic barium salts which enhanced X-ray attenuation in the body zones into which they distributed. More recently the field of X-ray contrast agents has been dominated by soluble iodine containing compounds such as those marketed by Nycomed AS under the trade names Omnipaque and Amipaque.

Much recent work on X-ray contrast agents has concentrated on aminopolycarboxylic acid (APCA) chelates of heavy metal ions and, recognising that effective imaging of many body sites requires localization at the body sites in question of relatively high concentrations of the metal ions, there have been suggestions that polychelants, that is substances possessing more than one separate chelant moiety, might be used to achieve this.

However we have now found that contrast enhancement may be achieved particularly effectively by the use of multinuclear complexes, that is complexes wherein the complexed moiety itself comprises two or more contrast enhancing atoms. Thus, for X-ray or ultrasound the complex would comprise two or more heavy metal atoms and for MRI the complex would contain two or more metal atoms with paramagnetic properties.

For the sake of clarity, the word "atom" is used to refer to ionic and covalently bonded forms and not simply to isolated uncharged atoms. Moreover it will be understood that the complexed moiety, while it is polynuclear, will not generally be so large as to be considered to be a particle itself. Thus it will generally have maximum dimensions 500 Å or less, e.g. of 80 Å or less, especially 40 Å or less. More particularly, the multinuclear entity will have a distinct, characteristic and reproducible overall structure and atom content and is thus quite distinct from a fragment or microcrystal of for example a metal oxide which in contrast will have a lattice containing very many of the unit cells of the crystal structure. The multinuclear entity on the other hand cannot itself be larger than the size of its unit cell.

Thus viewed from one aspect the invention provides a diagnostic imaging contrast medium comprising a physiologically tolerable multinuclear complex of formula I

$$(M_n B_u A_v)_x L_w \qquad (I)$$

(where $M_n B_u A_v$ is a multinuclear entity; each M which may be the same or different is a contrast enhancing metal atom covalently bonded to at least one atom B where u is non-zero; each B which may be the same or different is a non-metal bridging atom covalently bonded to at least two metal atoms M and optionally to further atoms; each A which may be the same or different is a non-metal non-bridging atom covalently bonded to a metal atom M; each L which may be the same or different is a ligand co-ordinately bonded to at least one metal atom M; n is a positive integer of value 2 or greater at least one metal atom M being tungsten or a lanthanide where n represents 2; u is zero or a positive integer, u being at least 2 unless n is at least 5 or at least one M is a lanthanide; x is a positive integer; and v and w are independently zero or positive integers; with the provisos that where n is 2 or 3 and no M is a lanthanide either at least one B is other than oxygen or sulphur or w is a positive integer and at least one L is a multidentate ligand other than EDTA) or a physiologically tolerable salt thereof, together with at least one pharmaceutical carrier or excipient.

Viewed from another aspect the invention provides the use of a multinuclear complex for the manufacture of a contrast medium as defined above for use in imaging of the human or non-human animal body.

Viewed from a still further aspect, the invention provides a method of generating an image of a human or non-human animal, preferably mammalian, body which method comprises administering to said body a physiologically tolerable contrast enhancing amount of a multinuclear complex as defined above and generating an image of at least part of said body into which said agent distributes, e.g. by X-ray, MRI, ultrasound, or scintigraphy.

Viewed from a further aspect the invention also provides a multinuclear complex, especially a complex of group Ib, IIb, IIIb, IVb, Vb, VIb, VIIb or VIII (CAS) metals, or lanthanides or actinides more especially group Vb, VIb, VIIb or VIII metals, particularly compounds having two or more atoms selected from Mn, Cr, Hf, Gd, Dy, Er, Ho, Tm, Yb, and Cu, and more preferably from V, Nb, Ta, Mo, W, Fe, Re, Tc, Ru and Rh, and especially preferably a tungsten and/or molybdenum complex, for use as a image contrast enhancing agent.

Viewed from a still further aspect the invention also provides a diagnostic imaging contrast medium comprising a multinuclear complex as defined above together with at least one sterile pharmaceutical carrier or excipient.

Multinuclear complexes have particular potential as contrast agents since, relative to mononuclear complexes such as the paramagnetic metal ion APCA chelates and polychelates conventionally proposed for use as X-ray contrast agents, the increase in the contrast enhancing atom content of the molecule is achieved with relatively little increase in the volume occupied by the contrast agent complexes, that is to say the use of multinuclear complexes enables a high ratio of contrast enhancing atom to overall complex volume to be achieved. Thus by increasing the relative content of contrast enhancing atoms in this way the total quantity of the contrast agent necessary in order to achieve the same contrast effect may be reduced and thus problems associated with contrast agent solubility or toxicity or with contrast medium viscosity may also be reduced.

As mentioned above, by multinuclear it is meant that the complexed moiety should comprise two or more contrast enhancing metal atoms (preferably in the form of a molecular ion). The multinuclear moiety also contains further atoms which may have little or no contrast enhancing effect but which may for example function as bridging atoms bonding the contrast enhancing atoms together. Particularly suitable examples of bridging atoms and groups include the atoms of groups IVa, Va, VIa and VIIa (CAS), e.g. oxygen, sulphur, selenium, tellurium, halogen atoms, nitrides, and bridging groups such as hydroxyl, carboxylates, alkoxy, aryloxy, phosphorus containing compounds and substituted nitrogen and phosphorus atoms, e.g. alkyl substituted nitrogen, phosphorus or P-oxide phosphorus atoms. The use of selenium and tellurium as bridging atoms, is especially attractive since the X-ray cross sections of these atoms, especially tellurium, are greater than those of the lower atomic weight sulphur, oxygen and nitrogen accordingly such atoms will contribute substantially to the overall X-ray attenuation by the complex. Carbonyl bridging groups are not favourable due to their inherent toxic effect in vivo and, advantageously the multinuclear complex will not contain such groups.

Preferably the complexed multinuclear moiety will contain at least 2, for example up to 100 (or even greater), especially up to 60, especially up to 50, for example up to 30, such as 2–15, especially 2 to 6, preferably 3 to 5 contrast enhancing metal atoms, particularly preferably 2, 3 or 4. The appropriate nature, e.g. the element, the isotope or the oxidation state, of the contrast enhancing metal atoms is of course dependent on the imaging technique in which the multinuclear complex is intended to function as a contrast agent. While generally speaking the multinuclear moiety will preferably contain at least two group Vb, VIb, VIIb or VIII atoms it may additionally contain other metal, especially transition metal, atoms and for X-ray imaging the multinuclear moiety will conveniently contain two or preferably three or more contrast enhancing atoms having atomic numbers of at least 37, preferably at least 50, while for scintigraphy the moiety will conveniently contain contrast enhancing atoms which are radioactive isotopes, e.g. radioactive metal ions, and for MRI the complex preferably contains paramagnetic metal atoms, especially lanthanide or first or second row transition metal atoms.

Examples of multinuclear complexes useful in MRI contrast agents include ferromagnetically coupled complexes such as have been reported by Harvey et al. Angew. Chem. Int. Ed. 30:598 (1991) (hexanuclear Fe(III) complexes with a S=5 ground state) and by Guillou et al. Inorg. Chem. 31:110 (1992) and Inorg. Chem. 29:1750 (1990) (a family of Gd(III)Cu(iI) complexes which are ferromagnetically coupled).

A ferromagnetically coupled paramagnetic complex useful for MRI contrast enhancement may thus take the form of a multinuclear complex containing two or more paramagnetic metal atoms selected from chromium, iron, nickel, manganese, cobalt, vanadium, molybdenum, tungsten, copper, platinum (particularly $^{195}$Pt), erbium, gadolinium, europium, dysprosium and holmium; with the metal atoms being stabilized in a ferromagnetic or superparamagnetic intramolecular complex configuration by an external complexing substance. The preferred metal ions include chromium, manganese, gadolinium, and iron, and the preferred external complexing substances includes organosulfates and their derivatives, carboxylic acids, and especially acetate ions, aminocarboxylates, etc. The ferromagnetically coupled, paramagnetic complex preferably has a net nuclear spin of greater than about ½ and has more than about 5 unpaired electrons. It should also preferably contain labile water groups.

For use as an X-ray contrast agent, it will generally be preferred that the multinuclear moiety should contain two or more heavy metal atoms, e.g. lanthanide, transition metal or other metal atoms such as for example Gd, Ce, Sr, Y, Zr, Tc, Ru, Rh, In, Ta, Nb, Dy, Hf, W, Mo, Re, Os, Pb, Ba, Bi, Ga, Sn, Hg and Tl. Advantageously the multinuclear complex comprises at least one metal ion selected from W, Mo, Re, Rh, Tc, V, Nb, Ru and Re, however Mo and W are particularly preferred. The choice of heavy metal used in the multinuclear complexes will be determined by a variety of factors including the toxicity of the overall complex and the X-ray absorption characteristics of the heavy atom. In this regard it should be noted that while the X-ray absorption cross section for atoms generally increases with increasing atomic number, the absorption cross section is itself dependent on the X-ray wavelength and increases with increasing photon energy until slightly above a value termed the K-edge whereafter attenuation decreases. Thus there are photon energy ranges for which one element is a better X-ray attenuator than a second even though outside these ranges the second element may be the better attenuator. Consequently the multinuclear complexes according to the invention will each have optimum photon energy ranges making them particularly suitable for operation with X-ray imaging apparatus utilizing X-rays having such photon energy ranges. However, by choosing multinuclear complexes containing atoms of more than one heavy element one may create X-ray contrast agents having optimal performance in more than one photon energy band or over a broader band. The complexes used according to the present invention are thus particularly attractive since they can be selected so as to match their X-ray attenuation profiles with the X-ray emission profiles of particular X-ray sources - in effect the invention provides "tunable" X-ray contrast media.

In formula I above, n, u and v are preferably 2 to 100, e.g. 2–50, particularly 2–30, especially 2 to 10, particularly 2 to 8 and especially preferably n and also preferably u are at least 3, particularly at least 4; x is preferably 1 to 20, especially 1 to 10, and particularly 1. The value of w depends on the size and identity of the ligand - nonetheless w is preferably 1 or 2, especially 1.

Non-chelant complexing agents, such as amines and mono carboxylic acids, e.g. acetic acid and amino acids, optionally substituted aromatic amines (such as pyrazole or pyridine), phosphines (e.g. alkyl and/or aryl phosphines), phosphites, phosphates, phosphonates and phosphinates are known and may be used in the formation of the multinuclear complexes of the invention. However since many of the contrast enhancing multinuclear entities are extremely toxic it is clearly preferable that the formation constants of the multinuclear complexes should be as high as possible and accordingly it is particularly preferred that the multinuclear moiety should be bound in a chelate complex. In a chelated multinuclear complex, L may conveniently represent a linear, branched or cyclic polyamino, polyaminocarboxylic or polycarboxylic acid.

More specifically, L may be represented by the formula.

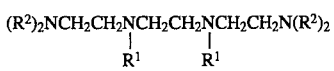

where $R^1$ which may be the same or different represents $R^2$, $C_{1-4}$hydroxyalkyl, carboxy-$C_{1-4}$alkyl or amino-$C_{1-4}$ alkyl groups or together both $R^1$ groups represent a group $CH_2CH_2NR^3CH_2CH_2$ where $R^3$ is an $R^2$ group or a $C_{1-4}$ alkyl group optionally substituted by hydroxyl, carboxyl, aryl or amino groups, each $R^2$ independently represents a hydrogen atom or an optionally amidated or esterified carboxy $C_{1-4}$ alkyl group, wherein any amine nitrogen is substituted by group selected from hydrogen atoms and optionally hydroxylated $C_{1-4}$ alkyl groups.

For example, L may be selected from

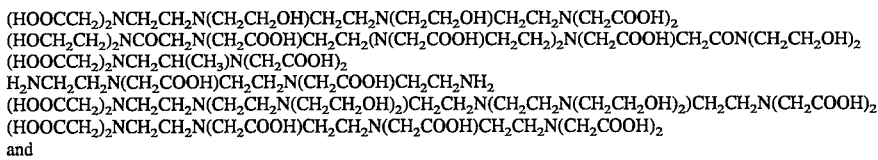

and

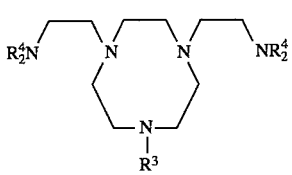

where each $R^4$ is hydrogen or carboxymethyl and $R^3$ is hydroxyalkyl or N-carboxymethylated amino alkyl.

The multinuclear complex used according to the invention may be ionic or, more preferably, may carry no net charge; most preferably the complex is non-ionic. Moreover it may be water-soluble or, less preferably, water-insoluble. Any necessary counterions should of course most preferably also be physiologically tolerable.

The range of physiologically acceptable counterions for therapeutically active agents is of course well known to pharmacologists.

Suitable countercations include for example protons, alkali and alkaline earth metal ions, e.g. sodium, calcium and magnesium and zinc, ammonium and organic cations (e.g. organic amine cations, quaternary ammonium, pyridinium, meglumine, alkylammonium, polyhydroxy-alkylammonium, basic protonated amino acids, etc), transition metal complex cations, organometallic cations, etc. Suitable counteranions include for example halide (e.g. chloride, bromide, iodide, $I_3$ Other suitable chelant moieties will be discussed in greater detail later.

Many multinuclear complexes are known and attention is drawn for example to the following publications: Chisholm, Trans. Met. Chem. 3: 321 (1978); Lee et al., Ang. Chem. Intl. Ed. Eng. 29: 840–856 (1990); the Abstracts of the 5th International Conference on the Chemistry and Use of Molybdenum, 1985, page 133; Novak et al., J. Inorg. Nucl. Chem. 36: 1061–1065 (1974); Bürgi et al. , Inorg. Chem. 20: 3829–3834 (1981); Chaudhuri et al., Z. anorg. allg. Chem. 521: 23–36 (1985); Ikari et al., Inorg. Chem. 29: 53–56 (1990); Tomohiro et al., J. Chem. Soc. Dalton Trans. (1990), 2459–2463; Henkel et al. , J. Chem. Soc. Dalton Trans. (1990), 1014–1016; Barbaro et al. JACS 112: 7238–7246 (1990); Richens et al., Inorg. Chem. 28: 1394–1402 (1989); Saito et al., Inorg. Chem. 28: 3588–3592 (1989); J. Chem. Soc. Dalton Trans (1990), 1765–1769; Inorg. Chem. 27: 3626–3629 (1988); JACS 108: 2757–2758 (1986); JCS Dalton (1978) 95–99; Inorg. Chem. 30: 1575–1579 (1991); Inorg. Chem. 18: 1621–1626 (1979); JACS 99: 4168–4170 (1977); Inorg. Chem 16: 2538–2545 (1977); Inorg. Chem 28: 1248–1254 (1989); Inorg. Chem. 15: 596–601 (1976); JACS 109: 3495–3496 (1987 ); JCS Dalton (1991) 57–59; JACS 112: 7402–74103 (1990); JACS 110: 1646–1647 (1988); Inorg. Chem. 28: 3588–3592 (1989); "Superconductivity in Ternary Compounds I", Ed. Fischer et al, Springer Verlag, Berlin, 1982; Inorg. Chem. 9: 1354–1360 (1970); JCS (1960) 1007, (1960) 3106, (1961) 750, (1962) 410, (1963) 4183 and (1964) 1287; Inorg. Chim. Acta 116:L25–L27 (1986); JCS Chem. Comm. (1985) 953–954; Inorg. Chem. 25: 3529–3532 (1986); JACS 106: 789–791 (1984); Angew. Chem. Int. Ed. Engl. 21: 795–796 (1982); JCS Chem. Comm. (1983) 1395–1397; Inorg. Chem. 30: 574–577 (1991); JACS 107: 6735–6736 (1985); Inorg Chem 29: 5120–5125 (1990); Inorg. Chem. 30: 2693–2699 (1991); JACS 100: 5252–5253 (1978); Angew Chem. Int. Ed. Engl. 19: 72–73 (1980); JACS 106: 1849–1851 (1984); Russ. J. Inorg. Chem. 31: 1429–1431 (1986); Inorg. Chem. 28: 2623–2630 (1989); JACS 108: 2757–2758 (1986); Polyhedron 5: 357–361 (1986); JACS 106: 2710–2711 (1984); Inorg. Chem. 16: 2538–2545 (1977); JCS Chem. Comm. (1985) 1437–1439; Inorg. Chem. Acta 113: L19–L21 (1986); Inorg. Chem. 30: 1687–1688 (1991); JACS 107: 6734–6735 (1985); Z. Naturforsch 34B: 434–436 (1979); Inorg. Chem. Acta 169: 235–243 (1990); JACS 108: 6430–6431 (1986); JACS 100: 7786–7787 (1978); Inorg. Chem. Acta 167: 39 (1990); Inorg. Chem. Acta 102: L25–L27 (1985); Inorg. Chem. 28: 3799 (1989); Inorg. Chem. 20: 3064 (1981); Inorg. Chem. 22: 2801 (1983); Inorg. Chem. 25: 3529 (1986); Inorg. Chem. 21: 1311 (1982); JCS Dalton (1978) 95; Z. Naturforsch 33B: 331 and 1398 (1978); JCS Dalton (1990) 3101; Science 228: 533 (1985); Tsigdinos "Heteropoly compounds of molybdenum and tungsten" Molybdenum Chemicals, Chemical Data Series Bulletin Cdb-12a, Nov. 1969, pp. 1–24, Climax Molybdenum Company, Connecticut, USA; "Heteropoly and isopoly oxometalates" M. T. Pope, Springer Verlag, NY, (1983); Angew Chem. Int. Ed. Engl. 18: 158 (1979); Angew. Chem. Int. Ed. 30: 1139–1141 (1991); J. Chem. Soc., Chem. Commun. (1991) 1453–1455; Angew. Chem. Int. Ed. 30: 688–689 (1991); Ibid., (1991) 598–600; Inorg. Chem. , (1992) 31: 110–114; Ibid., (1991) 30: 4963–4968; Ibid., (1991) 30: 4960–4962; Ibid., (1991) 30: 4968–4978; Ibid., (1990) 29: 1750–1755; Polyhedron, Vol. 8, No. 12, pp. 1531–1536 (1989); J. Am. Chem. Soc., (1991) 113: 7940–7944; Science, 241: 1479–1481 (1988); Polyhedron 10: 2203–2215 (1991) and Coordination Chem. Revs. 46: 245–280 (1982) and references cited therein.

Thus, for example, a simple multinuclear complex of formula I can be represented as follows:

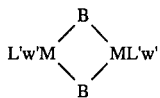
(II)

(wherein each M and L are as hereinbefore defined, each L', which may be the same or different is a ligand, either a molecule, an ion or one liganding moiety of a multidentate ligand; and W are each zero or positive integers).

Several L' groups can of course be provided by one chelant (L) and the metal atoms may be covalently bound to further atoms (generally designated by the letter A in the formulae referred to herein) not indicated by L, L or B and which function neither as ligands nor as bridges.

The M-B bonds to the bridging atoms B of formula II may be dative rather than covalent bonds. Examples of such complexes thus include the macrocyclic binuclear chelates such as those of formula III

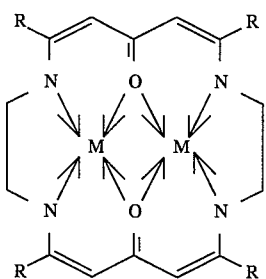
(III)

where each R which may be same or different is hydrogen or an organic group and each M is as defined above, for example a metal atom or ion, e.g. Ni, Pb(II) or Cu(II).

While the use of multinuclear complexes wherein the metal atoms M are not linked by covalent bonds does fall within the scope of the invention, it is particularly preferred that the multinuclear complexes be of the bridged type wherein the metal atoms M are covalently linked via bridging atoms or atom pairs (e.g. $S_2$ bridges) or bridging ligands (eg. acetate, hydroxo etc.). Of this category many polyoxoanions (and group VIa analogues) are known and they and complexes thereof are useful according to the invention, especially as X-ray contrast agents. Many such complexes are known and typical exemplary structures include the bi-, tri-, tetra- and hexa- nuclear structures of formulae II, IIIa, IV and V

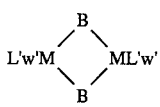
(II)

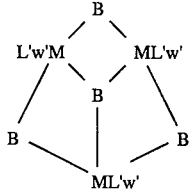
(IIIa)

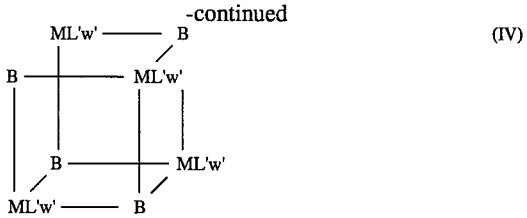
(IV)

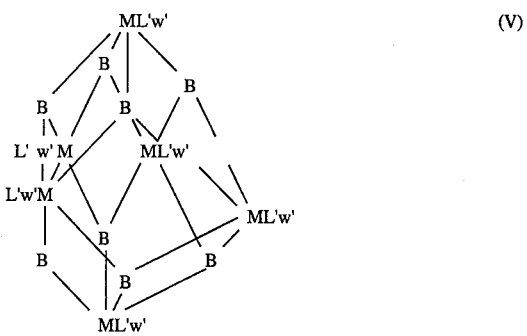
(V)

(wherein each B, M, L' and w' are defined above and where other non-bridging atoms covalently bonded to metals M are omitted for the sake of clarity). By way of example M may represent Mo, W, Re, Tc, V, Nb, Ta, Ru or Fe, but it is also possible for one (or more) of the metals M to be replaced by a transition or other metal, e.g. Hg, besides those metals specifically listed above in such a case however the substitute metal should be in a minority. These bi, tri, tetra and hexanuclear clusters of formula $M_2B_2$, $M_3B_4$, $M_4B_4$, and $M_6B_8$ are well described in the literature. A broad range of such $M_{2-50}$ clusters, e.g. $M_2$, $M_3$, $M_4$, $M_5$, $M_6$, $M_7$, $M_8$, $M_9$, $M_{10}$, $M_{11}$, $M_{12}$, $M_{17}$, $M_{18}$, $M_{36}$ and $M_{48}$ clusters, are known from the literature, especially where two or more of the M atoms are group Vb, VIb, VIIb or VIII metals. See for example Inorg. Chem. 9: 1354–1360 (1970); J. Chem. Soc. A. (1970) 2421; JCS Dalton Trans. (1975) 1526–1530; Inorg. Chem. 16: 2538–2545 (1977); JACS 99: 4168–4169 (1977); J. Inorg. Nucl. Chem. 16: 1061–1065 (1974); Inorg. Chem. 28: 447–451 (1989); Chem. Letters (1987), 2327–2330; J. Chem. Soc. Dalton Trans. (1987) 1163–1167; Inorg. Chem. 23: 4265–4269 (1984); Inorg. Chem. 24: 2950–2952 (1985); C. R. Seances Acad. Sci., Ser. C. (1966) 262, 1524; JACS 106: 2710–2711 (1984); J. Chem. Soc. Chem. Comm. (1985) 953; JACS 107: 5565 (1985); Inorg. Chem. 27: 3626–3629 (1988); J. Chem. Soc. Dalton Trans. (1990) 1765–1769; JACS 108: 2757–2758 (1986); JACS 104: 6781–6782 (1982); JACS 106: 789–791 (1984); JACS 107: 6734–6735 (1985); Inorg. Chim. Acta 116: L25L 27 (1986); JACS 105: 3905–3913 (1983); J. Chem. Soc. Chem. Comm. (1990) 1014–1016; JACS 112: 7238–7246 (1990); JACS 110: 1646–1647 (1988); J. Chem. Soc. Dalton Trans. (1991) 51–59; Inorg. Chem. 17:3245 (1978); J. Electroanal. Chem. and Interfacial Electrochem 54: 197–207 (1974); Z Naturforsch B33:1347 (1978); and Inorg. Chem. 28: 3588–3592 (1989).

The complexes above may be electrically charged or neutral - for administration as contrast agents they may preferably be complexed with ligands/chelating agents which serve to improve water solubility and to reduce toxicity and to leave unaffected, to only slightly increase or, most preferably, to reduce the magnitude of the overall electronic charge carried by the complex and stabilize redox sites of clusters.

In the case of bridged structures of these four formulae, the structural formulae can conveniently be written $M_2L_q(\mu_2B)_2$ and $M_3L_r(\mu_3B)_3$, $M_4L_s(\mu_3B)_4$ and $M_6L_t(\mu_3B)_8$ respectively ($\mu_3B$ indicating that the B is a bridging atom bonded to 3 metals, and q, r, s and t respectively being integers identifying the total number of complexing moieties). As mentioned above, it is particularly preferred that the multinuclear complexes be chelate complexes and it is especially preferred that a single multidentate chelant be used to coordinate at least two and preferably all of the liganded centres. A multidentate chelant L coordinating for example three metals would be referred to in these formulae as ($\mu_3L$).

Thus, for example, a multinuclear entity of formula I can comprise a unit of formula $M_3(\mu_3B)(\mu_2B)_3$, $M_4(\mu_3B)_4$ or $M_6(\mu_3B)_8$ (wherein M and B are defined above, but advantageously each M may indpendently represent Mo or W, and each B may independently represent O, S, Se or Te or a nitrogen or phosphorus atom covalently bonded to a proton or an organic group).

Particularly preferred multinuclear complexes suitable for use in a contrast medium according to the invention include the APCA chelate complexes of mixed or non-mixed polynuclear (where n=2, 3, 4, 6 or 12) oxides, sulphides, selenides and tellurides of molybdenum and/or tungsten, e.g. APCA chelates of multinuclear entities of formula

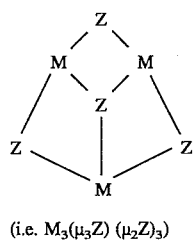

(i.e. $M_3(\mu_3Z)(\mu_2Z)_3$)

(VI)

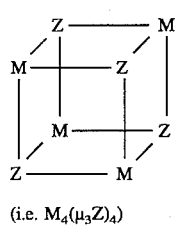

(i.e. $M_4(\mu_3Z)_4$)

(VII)

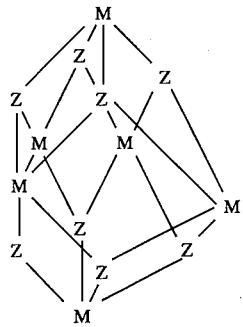

(i.e. $M_6(\mu_3Z)_8$)

(VIII)

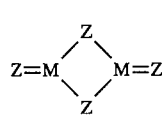

(i.e. $M_2Z_2(\mu_2Z)_2$)

(IX)

where each M is independently W or Mo and each Z is independently O, S, Se, Te, Cl, Br or I, e.g. $W_2S_2(\mu_2S)_2$, $W_2O_2(\mu_2O)(\mu_2S)$, $W_2O_2(\mu_2S)_2$, $MoWo_2(\mu_2O)_2$, $Mo_2O_2O_2(\mu_2O)_2$, $Mo_2O_2(\mu_2S)_2$, $W_4(\mu_3S)_4$, $W_3(\mu_3S)(\mu_2S)_3$, $W_3(\mu_3Se)(\mu_2Se)_3$, $W_3(\mu_2Te)(\mu_2Te)(\mu_2Te)_3$, $W_4(\mu Se)_4$, $W_4(\mu_3Te)_4$, $Mo_3(\mu_3Se)(\mu_2Se)_3$, $Mo_4(\mu Se)_4$, $Mo_2O_2(\mu_2Se)_2$, $Mo_3(\mu_3O)(\mu_2O)_3$, $W_6(\mu_3S)_8$, $MoWO_2(\mu_2O)(\mu_2S)$ $W_2O_2(\mu_2O)_2$ and $W_3(\mu_3X)_8$ (where X= Cl, Br, I).

Many of these multinuclear clusters are known from the literature cited above—the others may be prepared using methods analogous to those described in the literature.

Particularly preferred multinuclear clusters of type $M_2B_2$ include those of formula:

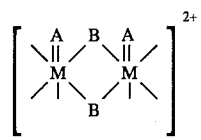

In the formula above, M preferably represents Mo, W or Re, whilst B and A preferably each represent O, S, Se or Te.

Specific examples of multinuclear cluster of this type include:

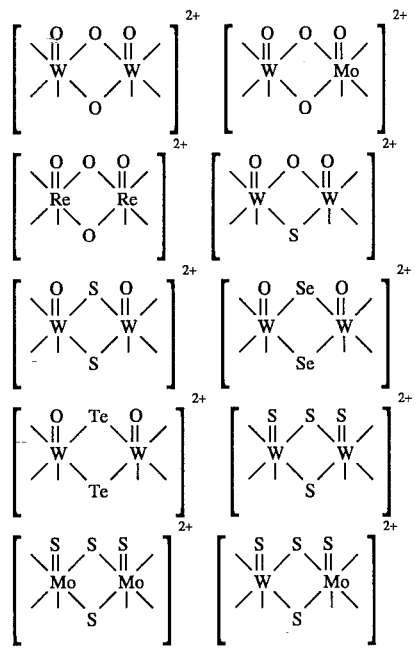

In the multinuclear clusters illustrated L is preferably

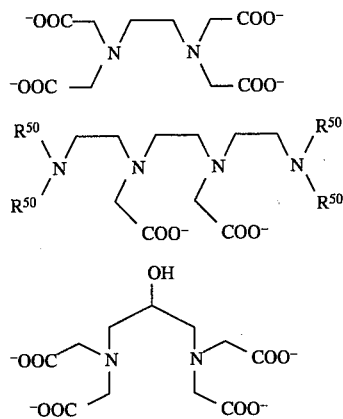

-continued

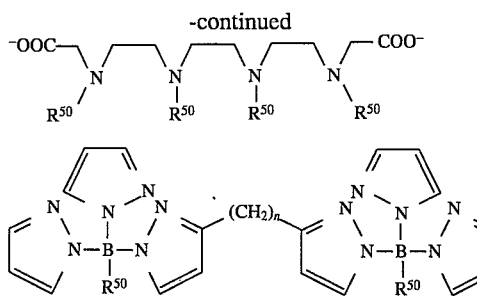

wherein each $R^{50}$ may represent a hydrogen atom or a straight chained or branched alkyl group optionally substituted by hydroxy, thiol, alkylthiol groups or by a carbonyl group which may itself be optionally alkyl substituted on the amide nitrogen. Preferably $R^{50}$ represents a $C_{1-6}$alkyl, optionally substituted as described above. More preferably $R^{50}$ may represent an alkyl group of formula

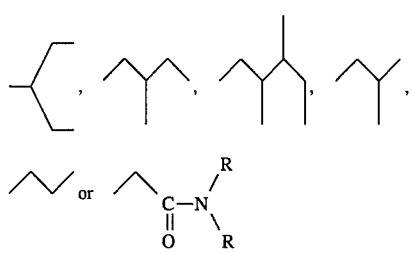

each of which may be substituted as described above.

For multinuclear clusters of type $M_2B_1$, the following general formula is preferred

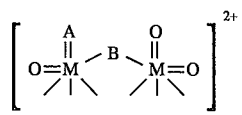

Again, M preferably represents Mo, W or Re, and A and B each preferably represent O, S, Se or Te. Preferably example of multinuclear clusters of this formula include

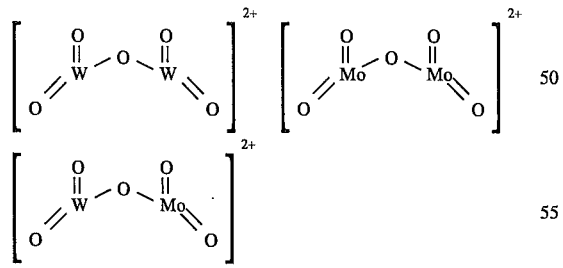

The multinuclear clusters described above are preferably chelated by ligands which are carbohydrates, for example sugar alcohols, especially those with a backbone chain containing of from 4 to 7 carbon atoms. Particularly preferred sugar alcohols include perseitol, galactitol, D-mannitol, erythritol, D-threitol, p-arabinatol, xylitol, ribitol and D-glucitol.

Preferred $M_3B_4$ multinuclear clusters may be represented as

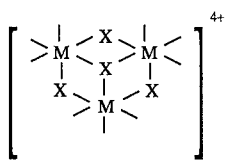

wherein each M is preferably Mo, W or Re and each B is preferably O, S, Se or Te. Examples of such clusters include

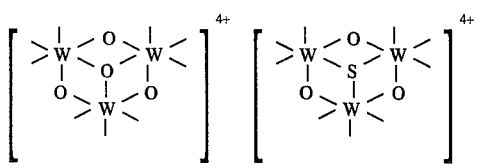

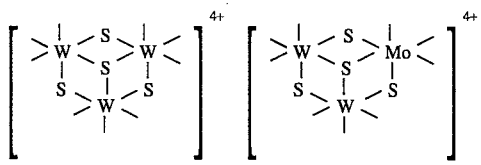

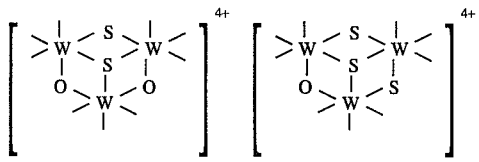

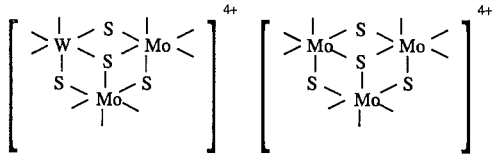

Preferred ligands for the $M_3B_4$ clusters include those of formula

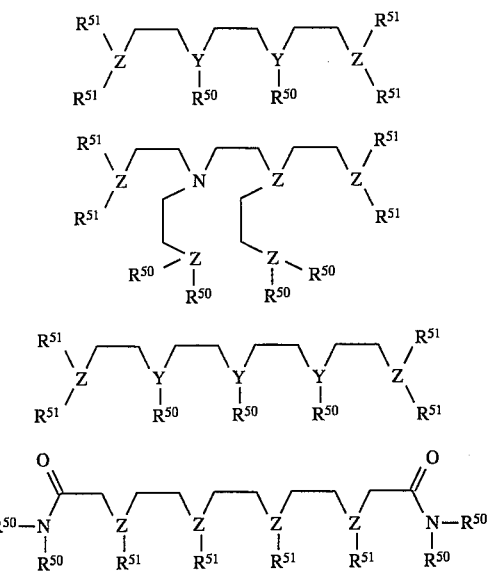

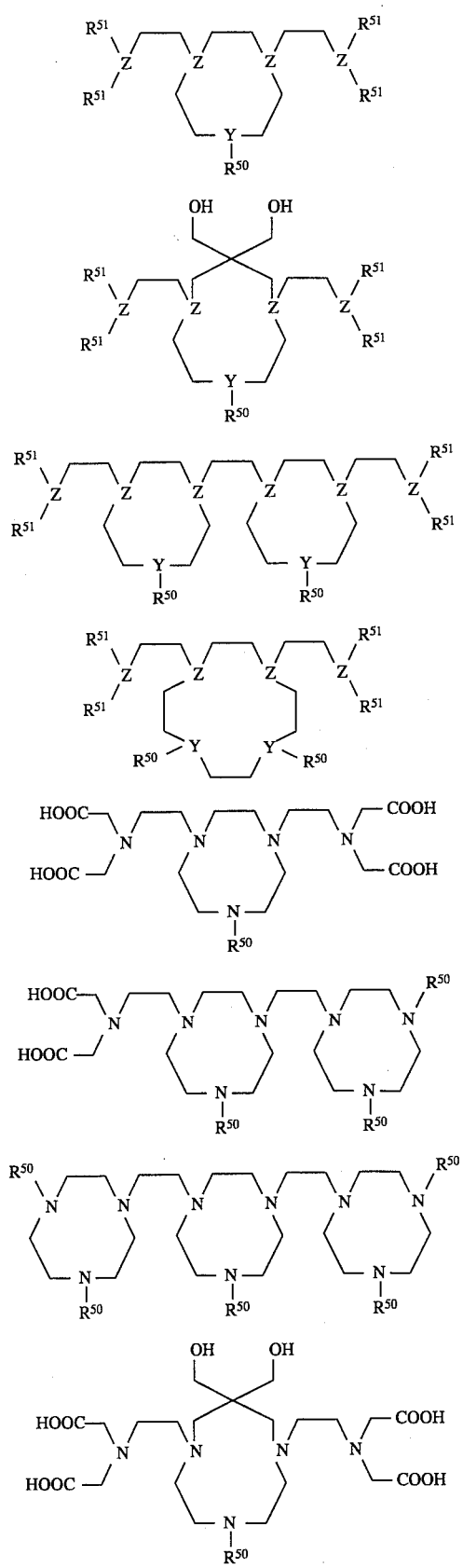

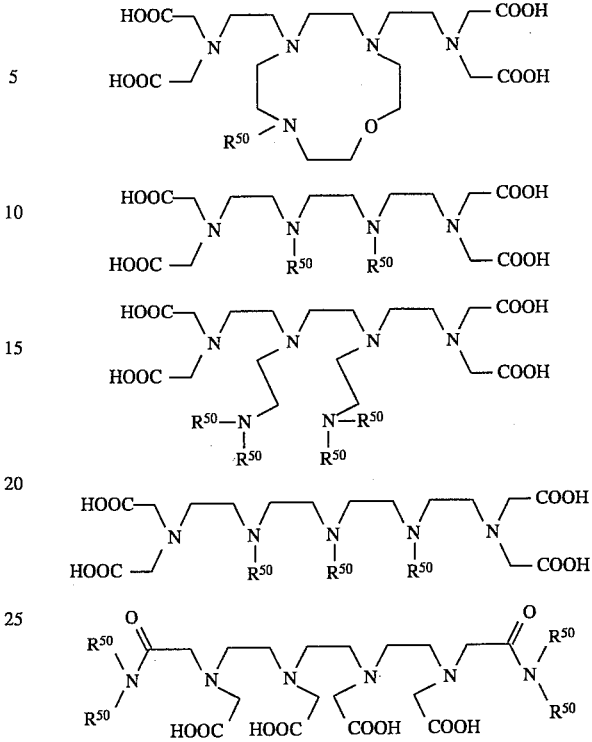

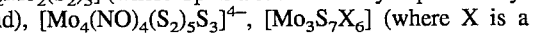

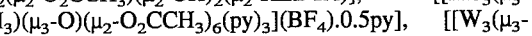

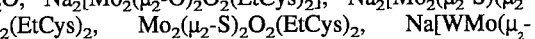

wherein each Z may represent a nitrogen or phosphorous atom; each Y may represent a nitrogen, phosphorous, oxygen or sulphur atom or a group $NR^{50}$ or $PR^{50}$ (where $R^{50}$ is as defined above) and each group $R^{51}$ may represent a group

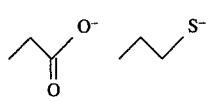

Examples of particular multinuclear entities known from the literature include:

$[W_3(\mu_{3-S})(\mu_2-S)_3(NCS)_9]^{5-}$, $[Mo_3(\mu_3-S)(\mu_2-S)_3(CN)_9]^{5-}$, $[N(C_2H_5)_4]_2[Mo_3(\mu_3-S)(\mu-S)_3(SCH_2CH_2S)_3$, $[H_2[Mo_3(\mu_3-S)(\mu_2-S)_3(NCH_2CO_2)_3]^{3-}$, $[Mo_3M^3S_4(H_2O)_{10}]^{4+}$ (where $M^3$=Fe, Cu or Ni), $[(H_2O)_9Mo_3S_4MoS_4Mo_3(H_2O)_9]^{8+}$, $[Cp'_2Mo_2(S_2)_5]$ (where Cp' is a substituted cyclopentadienyl ligand), $[Mo_4(NO)_4(S_2)_5S_3]^{4-}$, $[Mo_3S_7X_6]$ (where X is a halogen), $[W_3O_3Cl_5(O_2CCH_3)_4(PBu_3)_4]$, $[W_3O_3Cl_5(O_2CCH_3)(PBu_3)_3]$, $K[Mo_2(\mu_2-O_2CCH_3)(\mu_2-OH)_2(\mu_2-EDTA)]$, $K_2[Mo_2(\mu_2-OH)_2(NCS)_2(\mu_2-EDTA)]$, $[Mo_2(\mu_2-O_2CCH_3)(\mu_2-OH)_2(\mu_2-HEDTA)]$, $[[Mo_3(\mu_3-CCH_3)(\mu_3-O)(\mu_2-O_2CCH_3)_6(py)_3](BF_4).0.5py]$, $[[W_3(\mu_3-O)(\mu_2-O_2CCH_3)_6(H_2O)_3(CF_3SO_3)_2]$, $[Mo_2(\mu_2-S)_2OS(S_2CN(C_2H_5)_2)_2]$, $[Mo_2(\mu_2-S)_2O_2(S_2CNEt_2)_2]$, $[Mo_2(\mu_2-S)_2S_2(S_2CNEt)_2]$, $[Mo_2(\mu_2-S)_2OS(S_2CN(n-C_4H_9)_2)_2]$, $[N(C_2H_5)_4]_2[Mo_2(\mu_2-S)_2S_2(S_2C_2H_4)_2]$, $Na_2[Mo_2(\mu_2-O)_2O_2(Cys)_2].5 H_2O$, $Na_2(Mo_2(\mu_2-O)(\mu_2-S)O_2(Cys)_2].4H_2O$, $Na_2[Mo_2(\mu_2-S)_2O_2 (Cys)_2].4H_2O$, $Na_2[Mo_2(\mu_2-O)_2O_2(\mu_2-EDTA)].H_2O$, $Na_2[Mo_2(\mu_2-O)(\mu_2-S)O_2(\mu_2-EDTA)].2H_2O$, $Na_2[Mo_2(\mu_2-S)_2O_2(\mu_2-EDTA)].2H_2O$, $Na_2[Mo_2(\mu_2-O)_2O_2(EtCys)_2]$, $Na_2[Mo_2(\mu_2-S)(\mu_2-O)O_2(EtCys)_2$, $Mo_2(\mu_2-S)_2O_2(EtCys)_2$, $Na[WMo(\mu_2-O)_2O_2(\mu_2-EDTA)].5H_2O$, $Na_2[Mo_2(\mu_2-O)_2(CyDTA)]$ (CyDTA=trans-1,2-cyclohexanediaminetetraacetic acid), $(CH_3C_6H_4SO_3)_8[(H_2O)_9Mo_3(\mu_3-S)_4Mo(\mu_3-$ S)$_4$Mo$_3$(H$_2$O)$_9$.18H$_2$O, Mo$_6$(μ$_3$-Te)$_8$, Mo$_{6-n}$Ru$_n$(μ$_3$-Te)$_8$ (wherein n=0.5, 1.0, 1.5), Mo$_{5.5}$Rh$_{0.5}$(μ$_3$-Te)$_8$, Mo$_6$O(OEt)$_{18}$, [Mo$_6$S$_8$(PEt$_3$)$_6$], [W$_6$S$_8$(PEt$_3$)$_6$]; [M$^4_x$Mo$_6$X$_8$] (where M$^4$=Pb, Sn, Cu, etc. and X=S, Se, Te), [W$_6$(μ$_3$-X)$_8$]X$_4$ (where X=Cl, Br, I), [Mo$_6$(μ$_3$-X)$_8$]X$_4$ (where X=Cl, Br, I), Na$_3$[Mo$_4$(μ$_3$-S)$_4$(EDTA)$_2$].10H$_2$O, Na$_2$[Mo$_4$(μ$_3$-S)$_4$(EDTA)$_2$].6.5H$_2$O, Ca$_3$[Mo$_4$(μ$_3$-S)$_4$(EDTA)$_2$]$_2$.26H$_2$O, K$_8$[Mo$_4$(μ$_3$-S)$_4$(CN)$_{12}$]4H$_2$O, [Mo(η-C$_5$H$_4$Pr$^i$)(μ$_3$-S)$_4$, [Mo$_4$O$_4$(μ$_3$-O)$_4$(OSi(CH$_3$)$_3$)$_4$(HN(CH$_3$)$_2$)$_4$], (NH$_4$)$_6$[Mo$_4$(μ$_3$-S)$_4$(NCS)$_{12}$].10H$_2$O, [Mo$_3$Fe(μ$_3$-S)$_4$(EDTA)$_2$], [Mo$_2$Ni(μ$_3$-S)$_4$(H$_2$O)$_{10}$](CH$_3$C$_6$H$_4$SO$_3$)$_4$.7H$_2$O, Ca$_{2.5}$[Mo$_3$Ni(μ$_3$-S) 4(HNTA)(NTA)$_2$Cl].14H$_2$O, Cs$_2$[Mo$_3$(μ$_3$-O)(μ$_2$-O)$_3$(C$_2$O$_4$)$_3$(H$_2$O)$_3$] .4H$_2$O.½H$_2$C$_2$O$_4$, K$_5$[Mo$_3$(μ$_3$-S)(μ$_2$-S)$_3$(CN)$_9$].3KCN.4H$_2$O, [(C$_2$H$_5$)$_4$N]$_2$[Mo$_3$(μ$_3$-S)(μ$_2$-S)$_3$(SCH$_2$CH$_2$S)], [Mo$_3$(μ$_3$-S)(μ$_2$-S$_2$)$_3$X$_4$ (where X=Cl, Br), Mo$_3$(μ$_3$-S)(μ$_2$-S)$_3$Cl$_4$(PPh$_3$)$_3$(H$_2$O)$_2$.3THF, Mo$_3$(μ$_3$-S)(μ$_2$-S)$_3$Cl$_3$((CH$_3$)$_2$PCH$_2$CH$_2$P(CH$_3$)$_2$)$_3$, W$_3$(μ$_3$-S)(μ$_2$-S)$_3$Br$_4$, (bpyH)$_5$[W$_3$(μ$_3$-S)(μ$_2$-S)$_3$(NCS)$_9$].3H$_2$O, Ca[Mo$_3$(μ$_3$-S)(μ$_2$-S)$_3$(NH(CH$_2$COO)$_2$)$_3$].11.5H$_2$O, Ba[Mo$_3$(μ$_3$-S)(μ$_2$-O)$_3$(NH(CH$_2$COO)$_3$)$_3$].10H$_2$O, Mg[Mo$_3$(μ$_2$-O)$_3$(μ$_3$-S)(EDTA)].6H$_2$O, (Me$_4$N)$_5$[Mo$_3$(μ$_3$-S)(μ$_2$-O)$_2$(μ$_2$-S)(NCS)$_9$], Na$_2$[Mo$_2$(μ$_3$-S)(μ$_2$-O)$_3$(CyS)$_2$].4H$_2$O, (PyH)$_5$[Mo$_3$(μ$_2$(μ$_2$-S)(μ$_3$-S)(NCS)$_9$.2H$_2$O, [Mo$_2$W(μ$_2$-S)$_3$(μ$_3$-S)(H$_2$O)$_9$](CH$_3$C$_6$H$_4$SO$_3$)$_4$.9H$_2$O, [MoW$_2$(μ$_2$-S)$_3$(μ$_3$-S)(H$_2$O)$_9$](CH$_3$C$_6$H$_4$SO$_3$)$_4$.9H$_2$O, Cs$_2$[Mo$_3$(μ$_3$-S)(μ$_2$-S)$_3$(H$_2$O)$_3$(C$_2$O$_4$)$_3$].3H$_2$O, (NH$_4$)$_2$[Mo$_3$(μ$_3$-S)(μ$_2$-S$_2$)$_3$(S$_2$)$_3$], [N(C$_2$H$_5$)$_4$]$_2$[Mo$_3$(μ$_3$-S)(μ$_2$-S$_2$)$_3$Br$_6$]⅓CH$_3$CN, [N(C$_2$H$_5$)$_4$]$_2$[Mo$_3$(μ$_3$-S)(μ$_2$-S$_2$)$_3$(C$_6$H$_4$O$_4$S)$_3$] (where R=Et), [W$_3$(μ$_3$O)$_2$(μ$_2$O$_2$CMe)$_6$(H$_2$O)$_3$]$^{2+}$, [W$_4$(μ$_2$O)$_6$Cl$_6$(H$_2$O)$_4$]$^{2-}$, [Mo$_4$(μ$_2$N)$_4$Cl$_2$(H$_2$O)$_4$], [W$_4$(μ$_3$S)$_4$(μ-dtp)$_2$(dtp)$_4$](where dtp= S$_2$P(OC$_2$H$_5$)$_2$), [Cu$_4$Gd$_2$Cl$_4$L$_8$(LH)$_4$(H$_2$O)$_4$].2Cl.H$_2$O (where L=deprotonated 2-hydroxypyridene and LH=2-hydroxypyridene), [Mn$_7$(trien)$_2$(dien)$_2$O$_4$(OAc)$_8$](PF$_6$)$_4$.2H$_2$O, [Fe$_6$(μ$_3$-O)$_3$(μ$_2$-OH)$_2$(1,1-bis(N-methylimidazol-2-yl)ethanol)$_2$(acetato-oxo)$_{10}$], [Gd$_2$(ox)][Cu(pba)]$_3$[Cu(H$_2$O)$_5$].20 H$_2$O (where ox=oxalato and pba=1,3-propylenebis (oxamoto)), Ce$_2$(OSiPh$_3$)$_6$, [Dy(hfac)$_3$Cu(satn)OH] (where hfac=hexafluoroacetylacetonate and Cu(satn)OH=[N-(3-aminopropyl)-salicylaldiminato]hydroxocopper (II)) and [N(C$_2$H$_5$)$_4$]$_2$[Mo$_3$(μ$_3$-S)(μ$_2$-S$_2$)$_3$(C$_4$H$_4$O$_4$S)$_3$].

The multinuclear entities useful according to the invention thus include many known polynuclear inorganic molecules and ions and complexes thereof (including complexes with organic species), including those known under the general term polyoxoanions. Such multinuclear entities can be described by the following general formula:

[M$_α$D$_{βG δ}$]$_ε$J$_κ$   (X)

where each M which may be the same or different represents a metal atom within the multinuclear entity (cluster), each D which may be the same or different represents a non-metal atom, molecule or ion within the multinuclear entity that is bonded to one or more metals M, each G which may be the same or different represents an atom, molecule, ion or metal complex coordinatively bound to the M$_α$D$_β$ entity to yield the charged or uncharged cluster M$_α$D$_β$G$_δ$, each J, which may be the same or different, is a physiologicaly tolerable counterion (e.g. an alkali metal, alkaline earth metal, ammonium, quaternary ammonium, organic amine etc. cation where the cluster is anionic), α and β are numbers having a value of at least 2, e.g. 2–100, ε is a positive number, and δ and κ are each zero or postive numbers.

In the case of multinuclear entities based on polyoxoanions (or analogues wherein oxygen is wholly or partially replaced by other group VIa or VIIa elements), at least two (and preferably the majority) of the M atoms will generally be group Vb, VIb, VIIb or VIII elements (e.g. V, Fe, Nb, Mo, Tc, Ru, Rh, Ta, W and Re, especially Nb, Ta, Re, Mo, V, W, particularly Mo and W) while other (minority) M atoms or M atom complex may be selected for example from a secondary group comprising other transition metals, group IIa elements and lanthanides as well as other diverse metals such as Be, Al, Si, Ge, Sn, etc. for example as mentioned by Tsigdinos (Supra) and Pope (Supra) and references cited therein. For such multinuclear entities, referred to hereinafter as "polyoxoanions and analogues", a preferred group is of formula

[X$^a_λ$M$^a_μ$M$^b_ρ$M$^c_σ$O$_τ$]$^{\phi-}$   (XI)

(wherein

X$^a$ is selected from B, Al, Si, Ge, P, As, Se, Te, S, I, Co, Mn, Cu, alkylphosphonate, arytphosphonate alkylarsonate and arylarsonate (and others as mentioned in Pope (Supra) and the references cited therein);

M$^a$, M$^b$, M$^c$ are independently selected from W, Mo, V, Nb, Ta and Re; λ, μ, ρ, σ, τ, and φ are zero or positive numbers; λ is zero for isopolyoxoanions and mixed isopolyoxoanions or is a positive integer for heteropolyoxoanions;

and μ+ρ+σ≧2).

The counter-cations for polyoxoanions can be protons, organic cations (e.g. Ph$^+$, CH$_3^+$, as in Ar Seidle et al, JACS 108: 6430–6431 (1986)), alkali metal cations, alkaline earth cations, transition metal cations, organometallic cations (example of these can be found in V. Day et al, Science 228: 533–541 (1985)), ammonium and alkyl and aryl quaternary ammonium or pyridinium cations and mixtures thereof.

Quaternary ammonium salts of polyoxoanions can be developed which display remarkable hydrolytic stability and are highly soluble in organic media. Organo-soluble salts (i.e. lipophilic) exist as an ion pair whereby the polyoxoanion is effectively coated with the greasy quaternary ammonium salt.

Lipophilic polyoxoanions and chelant complexes can be dissolved in suitable oils, placed inside cyclodextrins, incorporated into liposomes or micelles. An oil solution can be combined with water and emulsion stabilizers to form an emulsion which can be utilized as a GI x-ray contrast agent. Liposomal formulations are interesting as liver agents. Cyclodextrin formulations are potential intravascular agents.

Polyoxyanions are also formed when tungstate and molybdate (MO$_4^{2-}$ where M=W, Mo) react with polyalcohol compounds (carbohydrates, alditols, etc.). This reaction may be used as an analytical method for the separation and identification of sugars. Recently, there has been interest in understanding the structural and physical inorganic aspects of these complexes. Structural studies have shown that, in the case of molybdenum, polyoxyanions are formed where the polyalcohol ligand provides hydroxide coordinating groups attached to four adjacent carbon atoms in the ligand backbone as shown here for a generic polyalcohol ligand:

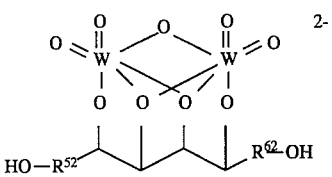

The complex is formed by a condensation process involving acid:

$$2MO_4^{2-} + \text{ligand} + 2H^+ \rightarrow M_2O_5(\text{ligand})^{2-} + 3H_2O$$

Potentiometric studies show that the metal-ligand binding constant approaches 20 for the strongest complexes with 15 being a typical value. The metal oxidation state is 6+ ($d^0$) and, as a result, the complexes are colorless. Due to both the fact that the complex is a salt and the polyhydroxy nature of the ligand, these metal-ligand complexes exhibit very high water solubility.

The use of these tungstate/molybdate-polyalcohol complexes as contrast agents for diagnostic x-ray imaging falls with the scope of the present invention. The high binding constants, high water solubility, and colorless nature of these complexes are ideal properties for x-ray contrast agents. Additionally, the coordinating ligands (polyalcohols, carbohydrates) are biocompatible. Higher cluster complexes may also be formed.

Although a large variety of polyoxoanions are known, these materials are almost exclusively salts containing discrete cations and anions (polyoxoanions). By changing the nature of the cation (organic vs inorganic) it is possible to modify the solubility proportions of the overall polyoxoanion complex (salt). The ability to modify the chemical/physical properties (charge, solubility, biocompatability) of such changes to polyoxoanions is important for their successful application as contrast agents and the literature indicates that modified polyoxoanions may be formed for example by the reaction of a reactive metal-organic complex with "defect" (substitutionally active) polyoxoanions (see JACS 101:759 (1979) and JCS Dalton, pages 1991-1997, (1991). For example, R*SiX*$_3$ (where R*=Et, CH=CH$_2$, C$_{10}$H$_{21}$, Ph; and X*=Cl, OEt) will react with [K]$_8$ [SiW$_{11}$O$_{39}$] to form [R"]$_4$[SiW$_{11}$O$_{40}$(SiR*)$_2$](R"=H$^+$, K$^+$, NR'$_4$; R'=Me, Bu) where the silicon atom is covalently bound to the polyoxometalate. This observed reaction can be used more generally to produce modified polyoxoanions such that the charge of the polyoxoanion, its solubility, or other desired physical/chemical properties can be systematically varied. Such complexes may obviate the need for separate counter-cations. These new polyoxoanions possessing the formula (X) as described earlier, are based on the use of substituted metal complexes G, such as C$_5$R'R"R"'R""R"""M' or (RO)$_3$M"R (M'=Ti$^{4+}$ and M"=Si$^{4+}$; R,R',R",R"',R""R"""=H, CH$_3$, alkyl, aryl, hydroxylated alkyls, amines, quaternary ammonium, APAC, etc.) where M' and M" complex react with and bind to the polyoxometalate. Proper choice of M' can lead to stable substituted polyoxometalates while proper choice of R can lead to changes in overall complex charge (osmolality), solubility, etc. For example, when R is a monoquaternary ammonium, then an electrically neutral polyoxoanion [SiW$_{11}$O$_{40}$(Si(CH$_2$)$_n$(NR$_3$))$_2$]$^0$ can be prepared. Such modified polyoxyanions may be attached to polychelants, for example the polychelants disclosed in WO-A-90/12050, WO-A-91/05762 and in Angew. Chem. Int. Ed. Engl. 29, pages 138-175 (1990) of Tomalia et al.

Similar neutral complexes can also be formed by judicious substitution of C$_5$R'R"R"'R""R""" groups coordinated to appropriate transition metals. The advantage of such complexes is a partial or complete reduction of the polyoxoanion charge and corresponding reduction of complex osmolality. Improved solubility and biocompatability may be realised by substitution with polyhydroxyl or polyaminepolyhydroxyl R groups.

A modified polyoxoanion may comprise one or more heteroatoms which displace the original metal atoms in the cluster so altering the characteristics of the heteropolyanions as discussed above. Suitable heteroatoms include Be, Y, La, Ti, Zr, Hi, V, Nb, Ta, Cr, Mo, W, Mn, Re, Co, Rh, Ni, Pt, Cu, Zn, B, Al, Ga, In, Tl, C, Si, Ge, Sn, P, As, Sb, S, Se, Te, I, Ce, Pr, Nd, Sm, Eu, Gd, Ho, Er, Yb, Th, U, Np and Am. Preferred heteroatoms include W, Mo, V, Ti, Sn, Nb, Rh, Ge, Re, Sb, V, Cr, Mn, Fe, Co, Ni, Cu, Zn, Al, Ga, In, Tl, Rh, Ru, Os, Ce, Pr, Nd, Sm, Eu, Ho, Th, U, Pt, Tb, Pu, Np, Am, Cm, Cf, La, Sr, Ba and Si.

Metal clusters, especially HPA's, which contain a mixture of heavy metals (which are contrast enhancing in X-ray imaging) and paramagnetic metals (which are contrast enhancing in MRI) are especially attractive. Amongst these particular emphasis may be given to those clusters in which the paramagnetic metals are in sites at or relatively close to the outer surface of the cluster, i.e. sites close enought to ambient water molecules to affect the MR signals therefrom. Clusters containing for example 10 to 20 heavy metals (such as Mo or W) and 1 to 4 paramagnetic metals (such as Gd, Mn, Fe or Dy) are especially interesting.

Particularly conveniently, the multinuclear entities are presented as their chelate complexes containing EDTA or other APCA's. Such chelate complexes are remarkably stable with regard to release of the heavy metal ions; thus W$_2$O$_2$(μ$_2$O)$_2$(μ$_2$EDTA), for example, has been found to have a thermodynamic stability constant in (log k) aqueous solution of about 29.1 (see Novak et al., J. Inorg. Nucl. Chem. 36: 1061∝1065 (1974)).

Besides EDTA, other chelants are suitable for the preparation of the multinuclear chelate complexes used according to the invention.

It is particularly preferred that the electrical charge carried by the complexing moieties should substantially if not completely balance that carried by the complexed entity; for APCA chelants this may easily be achieved for example by omission, replacement or deactivation (e.g. by ester or amide formation) of one or more of the carboxyl moieties.

Many suitable chelants are widely known or have been described in the literature, especially literature relating to heavy metal detoxification agents bifunctional chelants and chelate-based contrast agents, e.g. those described in WO-A-89/00557 (Berg) and the documents mentioned therein and in the search report appended thereto, U.S. Pat. No. 4,647,447 (Gries), U.S. Pat. No. 4,826,673 (Dean), EP-A-230893 (Felder), EP-A-217577 (Frincke), U.S. Pat. No. 4,652,519 (Warshawsky), U.S. Pat. No. 4,687,659 (Quay), and numerous other recent patent publications of Nycomed AS, Salutar Inc, Schering AG, Squibb, Bracco, Mallinckrodt, Dow and Guerbet.

The chelants useful for complexing the multinuclear moiety and which form coordinate bonds directly with the metals of the multinuclear moiety can be selected from a wide range of structures. Many of the most useful chelants are of general formula XII $$Z^3(X(CHR_1)_a)_bXZ^3 \qquad \text{(XII)}$$

(where a is an integer of from 2 to 12, preferably 2 to 10, e.g.

2, 3, or 4; b is an integer of from 1 to 8, preferably 2, 3 or 4;

each R, independently is hydrogen, a hydrophilic or linking group (e.g. a hydroxyalkyl group) or two groups $R_1$, or one $R_1$ and one group $Z^3$, together represent a saturated or unsaturated heterocyclic or carbocyclic ring, preferably with 5–7 ring atoms;

each X independently is O, S, $NZ^3$ or $PZ^3$, each $Z^3$ indpendently is hydrogen, hydroxyalkyl, mercaptoalkyl, carboxyalkyl (or an amide or ester derivative thereof e.g. —$CH_2CONHCH_3$) or optionally hydroxy or mercapto substituted acyl, or is a side chain $((CHR_1)_aX^*)_cZ^*$ (where c is 1 to 4 and $X^*$ and $Z^*$ are as defined for X and $Z^3$ but do not represent any group containing a $X^*$ or $Z^*$ group) or two groups $Z^3$ together form a briding group $((CHR_1)_a X^*)_c(CHR_1)_a)$ or are salts thereof).

While polyamines and polyethers, especially linear or cyclic polyamines and polyethers, such as ethylenediamine, 1,4,7-triazacyclononane and cyclen, can be used as chelants, in general APCAs and starburst dendrimers (see e.g. Tomalia, Angew. Chem. Engl. Ed. 29: 138–175 (1990)) are preferred, particularly DTPA, EDTA, TTHA and derivatives thereof and other cyclic and non-cyclic APCAs as defined in WO-A-89/00557 and APCAs of formula XIII

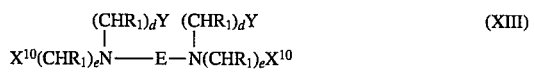

where each $R_1$ is independently hydrogen or an optionally hydroxylated and/or alkoxylated alkyl group or an organic side chain adapted for the attachment of or attached to a macromolecule;

d and e each is an integer having a value of 1, 2 or 3;

each $X^{10}$ is independently a carboxyl (i.e. COOH) or phosphate (i.e. $PO_3H_2$) group a derivative thereof;

each Y is independently a group $X^{10}$, $SR_1$, $OR_1$ or $N(R_3)_2$;

E is a group $(CHR_2)_f(X''(CHR_2)_f)_g$ where f is an integer of from 2 to 5, preferably 2 or 3, g is zero, 1 or 2, preferably zero or 1, each f preferably being 2 when g is non-zero, $X''$ is O, S or $N(CHR_1)_aY$, preferably O or S, each $R_2$ is independently $R_1$ or, when the carbon to which it is attached is not bonded to a nitrogen, hydroxyl, or two $R_2$ groups, especially where f is 2, may together with the intervening carbons form a cycloalkyl group optionally substituted by hydroxyl or R, groups, and each $R_3$ is independently a group $R_1$ or $N(R_3)_2$ represents a preferably saturated heterocyclic group preferably having 5 or 6 ring members, optionally containing as a further heteroatom a nitrogen or oxygen and optionally substituted by $R_1$ groups. It is also possible for the multinuclear moiety to be chelated by a chelant which is then itself attached to form part of an oligomer or polymer, such as a starburst dendrimer.

In the chelants of formula XII or XIII, any alkyl moiety preferably has a carbon atom content of up to 8, any cycloalkyl group preferably is a $C_{3-8}$, especially $C_{5-7}$, ring and any carboxyl derivative is preferably a $CON(R_3)_2$ or $CON(OH)R_1$ group.

Other suitable chelants include the pyrazole for example Prog. I1. (1986), in particular compounds of formula XIV

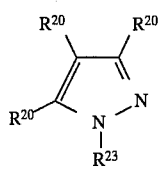

where $R^{20}$ and $R^{21}$, which may be the same different, represent hydrogen atoms or an optionally hydroxylated, optionally alkoxylated alkyl group (e.g. $C_{1-8}$alkyl), or a pyrazolyl group PZ of formula $MtR^{24}_3$ or

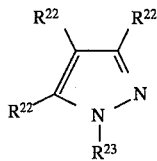

where one of groups $R^{22}$ and $R^{23}$ is a bond and the remaining groups $R^{22}$ and $R^{23}$ are groups as defined for $R^{20}$ and $R^{21}$ respectively but do not represent PZ groups, or one may represent bond or an alkylene chain (e.g. $C_{1-10}$ n-alkylene) linked to a group $R^{22}$ or $R^{23}$ of a further group of formula XIV (i.e. to form a dimer). Mt is B, Al or Ge, and $R^{24}$ is hydrogen, alkyl, amine, APCA or aryl (e.g. 5 to 8 ring membered homo or heteroaryl such as phenyl or pyrazolyl (e.g. PZ) group.

Of particular interest are the anionic ligands of formula XV

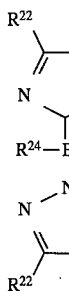

and the dimers thereof of formula XVI

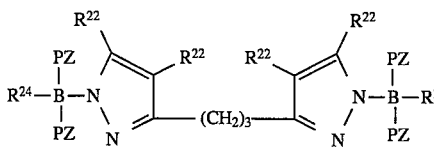

where Z is zero or a positive integer, e.g. 1–10. Higher oligomers, such as trimers, tetramers or polymers may also be formed in a similar fashion.

The trispyrazolylborate ligands have several features to recommend them for metal-ion cluster ligating groups. The molecule functions as a tridentate coordinating ligand that presents aromatic amine functionality for metal ion binding. These ligands are known for strong chelation to metal ions. Because of the four coordinate binding to boron, the ligand carries an uninegative charge. Therefore, this ligand can be used to introduce negative charge to a resulting cluster/ligand complex. This may be especially useful where use of the carboxylate ion is undesirable. Substitutions can occur both at the boron ion ($R^{24}$) and at the 3 ring positions ($R^{22}$, $R^{23}_b$) of PZ. This allows for the formation of a ligand which can be optimized by appropriate substitution for solubility and biocompatability properties (such as where $R^{22}$, $R^{23}$ or $R^{\cong}$ are polyhydroxylated). The poly(tris-pyrazolylborate) ligands moreover can form a single coordinating molecule capable of binding to more than one metal ion:

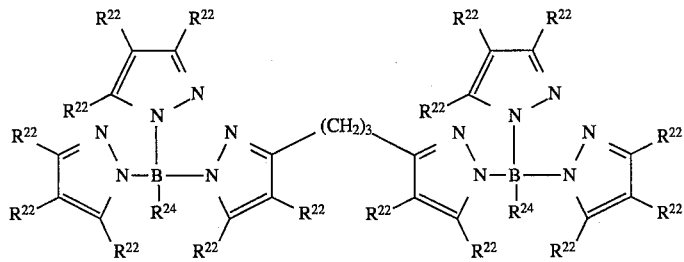

($Z \geq 0$) one application for this type of oligomeric tris-PZ ligand would be the formation of neutral tungsten dimers.

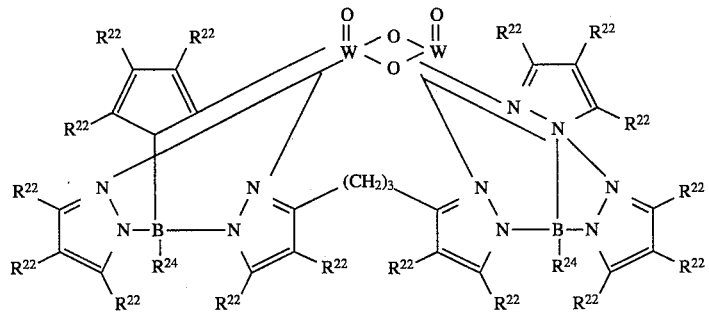

$Z \geq 0$).

Further Examples of suitable chelants include compounds of formulae:

| | |
|---|---|
| $(HOOCCH_2)_2NCH_2CH_2N(CH_2COOH)_2$ | (i) |
| $(HSCH_2CH_2)_2NCH_2CH_2N(CH_2CH_2SH)_2$ | (ii) |
| $H_2NCH_2CH_2N(CH_2COOH)CH_2CH_2N(CH_2COOH)CH_2CH_2NH_2$ | (iii) |
| $H_2NCH_2CH_2N(CH_2CH_2SH)CH_2CH_2N(CH_2CH_2SH)CH_2CH_2NH_2$ | (iv) |
| $HOOCCH_2(NCH_2CH_2)_3NCH_2COOH$ | (v) |
| $HSCH_2CH_2(NCH_2CH_2)_4SH$ | (vi) |

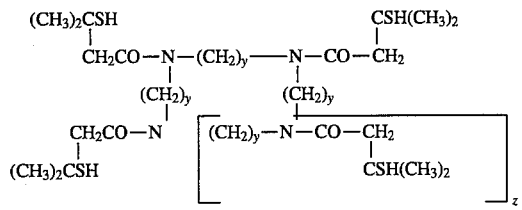

(vii)

(where y = is 1 or more, eg. 6, 7, 8, 9 or 10 and z = 0 or 1)

| | |
|---|---|
| $(HOOCCH_2)_2NH$ | (viii) |
| $(HSCH_2CH_2)_2NH$ | (ix) |
| $(HOOCCH_2)_2NCH_2CH_2N(CH_2COOH)CH_2CH_2N(CH_2COOH)CH_2CH_2N(CH_2COOH)_2$ | (x) |
| $(HSCH_2CH_2)_2NCH_2CH_2N(CH_2CH_2SH)CH_2CH_2N(CH_2CH_2SH)CH_2CH_2N(CH_2CH_2SH)_2$ | (xi) |
| $(HOOCCH_2)_2N(CH_2CH_2NH)_2CH_2CH_2N(CH_2COOH)_2$ | (xii) |
| $(HSCH_2CH_2)_2N(CH_2CH_2NH)_2CH_2CH_2N(CH_2CH_2SH)_2$ | (xiii) |
| pyridine-2,6-dicarboxylic acid | (xiv) |
| 2,6-bis-merceptomethyl-pyridine | (xv) |

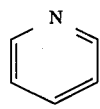

(xvi)

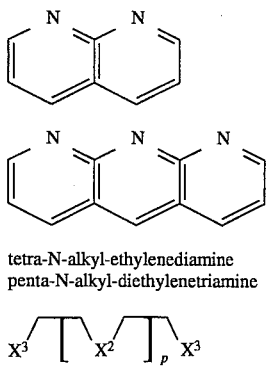

tetra-N-alkyl-ethylenediamine
penta-N-alkyl-diethylenetriamine

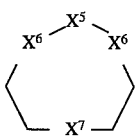

(where $X^3 = NR_2^{40}$ or $PR_2^{40}$ p=1, 2, 3 or 4

$X^2$=O, S or $NR^{41}$ $R^{40}$=CH$_2$COOH, CH$_2$CH$_2$SH, CH$_2$CH$_2$OH, CH$_2$PO$_3$H$_2$, $C_{1-6}$alkylamines, $C_{1-6}$alkylphosphines or substituted $C_{4-12}$ homo or heteroaryls $R^{41}$=CH(CH$_2$X$^4$)$_2$, CH$_2$CHX$^4$CH$^2$X$^4$, CH$_2$CHX$^4$CHX$^4$CH$_2$X$^4$, CH$_2$CHX$^4$CH$_3$, CH$_2$CH$_2$X$^4$, CH$_2$CONR$_2^{42}$ or substituted $C_{4-12}$ homo or heteroaryls $X^4$=OH, SH or SR$^{42}$ $R^{42}$=alkyl, e.g. $C_{1-6}$ alkyl, or substituted $C_{4-12}$ homo or heteroaryls and substituted aryl means subsituted by one or more groups selected from carboxyl (and derivatives thereof e.g. salts, amides and esters), hydroxyl, mercapto, phosphates, amines and phosphines).

(xxii)

(X$^5$=CH$_2$C(CH$_2$OH)$_2$CH$_2$ or CH$_2$CH$_2$

X$^6$=NR$^{40}$, PR$^{40}$, N(CH$_2$)$_2$X$^3$ or one X$^6$ may provide an alkylene chain (e.g. CH$_2$CH$_2$) linking the macrocycle to a similar macrocycle X$^7$=X$^2$ or X$^6$)

2-carboxypyridine (nicotinic acid) (xxiii) and the phosphorus analogues of the nitrogen-donor based ligands.

For M$_4$B$_4$ multinuclear complexes, e.g. W$_4$(μ$_3$B)$_4^{4+}$ (where B=S, Se, Te, O, halogen (e.g., Cl, Br, I),N-R$^{31}$ or P-R$^{31}$ (where R$^{31}$ is an appropriate substituent, e.g. hydrogen, aryl (e.g. phenyl), alkyl etc.), chelants (i) to (vii) (where z=1) are of particular interest; for M$_3$B$_4$ complexes, e.g. W$_3$(μ$_3$B')(μ$_2$B")$_3^{4+}$ (where B'and B" are S, Se, Te, O, halogen (e.g. Cl, Br. I), NR$^{31}$ or PR$^{31}$, B' preferably being S), chelants (vii) (where z=o) and (viii) to (xv) are of particular interest; and for M$_6$B$_8$ complexes, e.g. W$_6$(μ$_3$S)$_8$, chelants such as (xvi) to (xx) are of particular interest. For M$_2$B$_2$ complexes, e.g. W$_2$O$_2$(μ$_2$O)$_2^{2+}$ chelants such as NTA, IDA, EDTA, HEDTA, DTPA, DTPA-BMA, HEDDA, TTDA, EDTA-BMA, TBEDDA, MEEDDA, TTHA, EDDA, EHPG, PDTA, CHDTA, HPDTA, TACN, TTHA, CMPA-BMPA, DTPA-BMPA and triazacyclononane monoacetic acid, especially TTHA, are of particular interest.

For M$_4$B$_4$ and M$_3$B$_4$ multinuclear complexes, the use of macrocyclic chelants, e.g. those of formulae (vii) and (xxii)

(xvii)

(xviii)

(xix)
(xx)

(xxi)

and linear chelants of formula (xxi) is particularly preferred as a means by which to enhance solution stability.

Particularly preferred chelants include cyclen, TTHA, EDTA, DTPA, DOTA, DO3A, HP-DO3A, the 6-oxa and 6-thia analogues of DTPA and amides thereof, e.g. DTPA-BMA and DTPA-BMO (6-carboxymethyl-3,9-bis(morpholino-carbonyl-methyl)- 3,6,9-triazaundecanedioic acid - the Gd(III) chelate whereof is sometimes referred to as gadopenamide).

Besides the APCA chelants, particular mention can also be made of polyoxa/polyaza cycloalkane macrocyclic chelants, e.g. such as are described in U.S. Pat. No. 3,860, 611, U.S. Pat. No. 3,952,015 and JOC 22: 1029 (1957), JOC 39: 2351 (1974); JOC 40: 1205 (1975) and JOC 45: 1177 (1980).

The chelant may be attached directly or via a linking group to a hapten (i.e. a relatively small non-antigenic molecule such as cholesterol, heparin, etc.) or to a macromolecule (conveniently be any tissue, organ or cell targeting macromolecule, for example a biomolecule such as a protein, an antibody or antibody fragment, or alternatively a biologically relatively inert material such as a polysaccharide or poly-sugar alcohol, e.g. dextran, starch, cyclodextrin etc). Such macromolecules are discussed extensively in the recent literature relating to contrast agents.

The chelants of formulae XII and XIII are already known from the literature or may be prepared in analogous fashion to the known chelants. The preparation of chelants of formula XII and XIII will however generally fall into one of two categories: derivatization of a polyamine or amination of polyfunctional compounds. Derivatization can be performed in one or more stages and the groups introduced may, in intermediate or final stages, be subject to reduction or deprotection steps.

Thus for example starting from the linear polyamine

(where E' is (CHR$_2$)$_f$[X'''(CHR$_2$)$_f$]$_g$ and X'''is O, S or NH) derivatization may be effected by the following nonreductive or reductive reaction schemes:

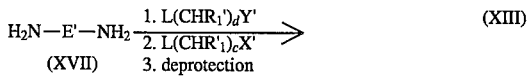

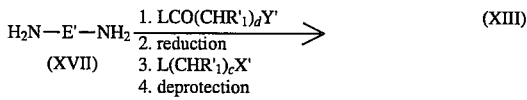

where L is a leaving group and R$_1$', Y' and X' are optionally protected $R_1$, Y and X groups.

Alternatively a bifunctional reagent of formulae $$L-E-L \qquad (XVIII)$$

or $$LCO.E''.CO.L \qquad (XIX)$$

may be aminated with or without a subsequent reduction step according to the following schemes:

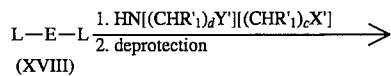

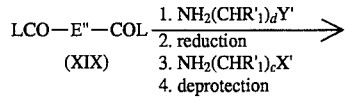

where E" is $(CHR'_1)_{f-h}[Z^3(CHR_1')_p]_i[Z^3(CHR'_1)_{f-1}]_j$ (where j is 0 or 1, h+j is 2, i is zero or the positive integer g−1) and L, $R'_1$, Y' and X' are as hereinbefore defined.

The polyamine starting materials are either available commercially or may be prepared by routine methods. Thus for example commercially suitable polyamines include $NH_2(CH_2)_{2-5}NH_2$, $NH_2(CH_2)_2O(CH_2)_2NH_2$, $NH_2CH_2CHOHCH_2NH_2$, $NH_2(CH)_2S(CH_2)_2NH_2$. Optionally substituted polyamines may also be prepared by methods described in or analogous to those of EP-A-287465 (Schaeffer), WO-A-89/00557 (Berg), Brechbiel et al. Inorg. Chem. 25: 2772 (1986), Yeh et al. Analytical Biochem. 100: 152 (1979), Vögtle et al. Liebigs Ann. Chem. (1977) 1344, Kasina et al. J. Med. Chem. 29: 1933 (1986), Bedell et al. Inorg. Chem. 21:874 (1982), etc.

Derivatization of the polyamines may be effected using alkylation agents such as those described by EP-A- 230893 (Felder), e.g. $HalCH_2COL''$, $HalCH(COOH)CH_2O$ Benzyl, or $HalCH(COOH)_2$ (where Hal is Cl or Br and L" is OH, NHAlkyl or NAlkyl$_2$ (e.g NHCH$_3$ or N(CH$_3$)$_2$) or HalCH$_2$NAlkyl$_2$ (e.g. ClCH$_2$N(CH$_3$)$_2$), followed where necessary by deprotection of protected groups. Examples of such schemes include

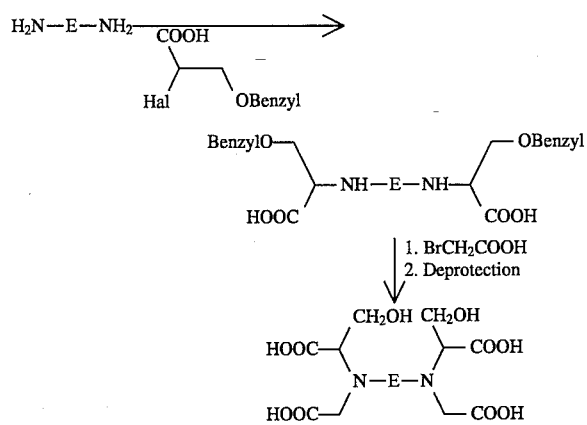

and

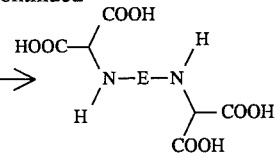

Selective alkylation of amines is described by Nordlander et al. Tetr. Lett. (1978) 4987 and J. Org. Chem. 49: 133 (1984) and by Aspinall et al. JACS 63: 852 (1941). Many other appropriate derivatization procedures are described in the literature.

For the reductive procedure discussed above, reaction may be of many of the same or similar polyamines with aldehyde, carboxyl or carboxyl derivative compounds followed by reduction of the amide carbonyl groups, e.g. using sodium cyanoborohydride or diborane, e.g. as in the scheme

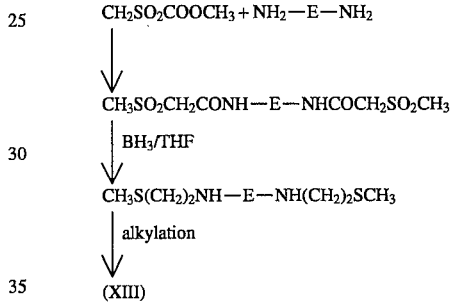

The resulting thioesters could equally be produced by reaction of an aminocarboxylic acid reagent with a chloroalkylsulphide, e.g.

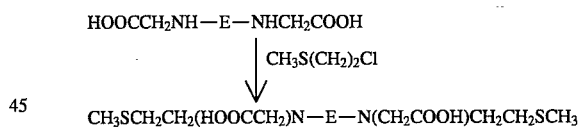

As mentioned above, the chelants of formula (XIII) can also be produced by amination of polyfunctional reagents. One example of this procedure is given by Huber et al. J. Chem. Soc. Chem. Comm. (1989) 879, i.e.

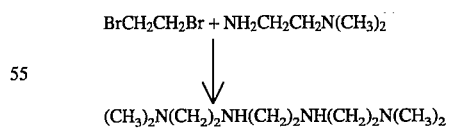

Amine intermediates can also be produced by hydrogenation of corresponding nitrile compounds.

The resulting polyamine can then be converted to a compound of formula XIII by reaction with $X^9CH_2CN$ (where $X^9$ is OH or, prferably, a halogen) followed by hydrolysis. A wide variety of other polyhalo and amine compounds suitable for use in such reactions are available commercially or may be prepared using text book methods.

In a similar manner, polyfunctional acids may be reacted with appropriate amines if necessary after activation of the acid groups, reduction of the amide and alkylation will yield chelants of formula XIII. Commercially available polyfunctional acids utilizable in this way include for example

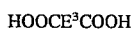

HOOCE³COOH where E³ is —CHOHCH₂CH₂—, —(CHOH)₂—, —(CH₂)₁₋₃— or

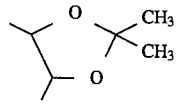

In order to attach the chelant to a macromolecule, e.g. a protein or a carbohydrate, the chelant may be provided with a reactive side chain (e.g. described by Meares et al. Anal. Biochem. 142: 68(1984), etc). Alternatively attachment can be efected for example using the methods developed by Salutar Inc. (See for example WO-A-90/12050 and Sieving et al., Bioconjugate Chem. 1: 65–71 (1990)) or the mixed anhydride or cyclic anhydride methods of Krejcarek et al Biochemical and Biophysical Research Comm. 77: 881 (1977) or Hnatowich et al. Science 220: 613 (1983) etc. Attachment of the chelant may be either directly to the macromolecule or, preferably, to an intermediate polymer, e.g. poly-L-lysine or polyethylene-imine, onto which a plurality of chelants may be loaded, e.g. as discussed in EP-A-331616 (Deutsch).

Thus for example the following macromolecule-linkable chelants are suggested in the literature:

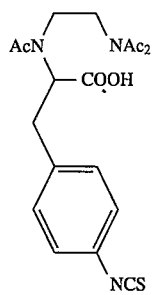

(Westerberg et al. J. Med. Chem. 32: 736 (1989))
(Ac = CH₂COOH)

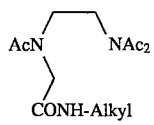

(JACS 59: S + D 10 (1982))

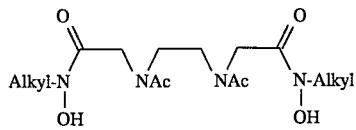

(Turowski et al. Inorg. Chem. 27: 474 (1988))

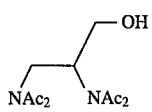

(Hernandez et al. An. Quim. Ser. B. 83: 172 1987))

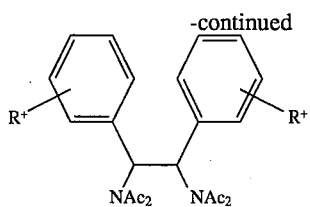

(Zupanc et al. Glas. Hem Technol. Bosne Hercegovine (1970)71)

(R⁺ = NO₂, OH)

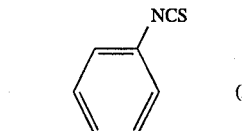

(EP-A-217577 (Frinke))

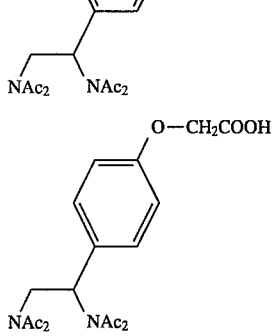

(J. Radiol. Chem. 53: 327 (1979))

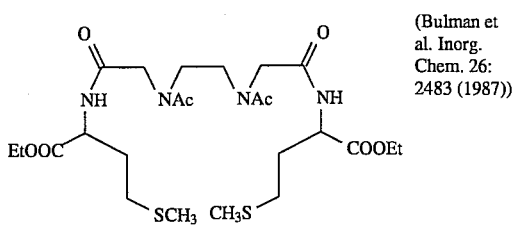

(Bulman et al. Inorg. Chem. 26: 2483 (1987))

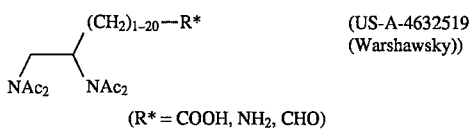

(US-A-4632519 (Warshawsky))

(R* = COOH, NH₂, CHO)

The tridentate tris-thiols of Holm et al. (see JACS 112: 8015–8023(1990) and JACS 110: 2484–2494 (1988)) also deserve particular mention, especially for the complexation of tetranuclear clusters.

Procedures for preparing linear, branched and macrocyclic chelants especially suited for M₄B₄ and M₃B₄ structures are exemplified by the following reaction schemes:

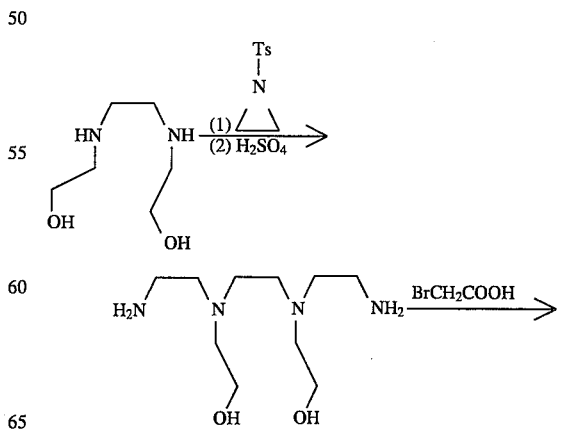

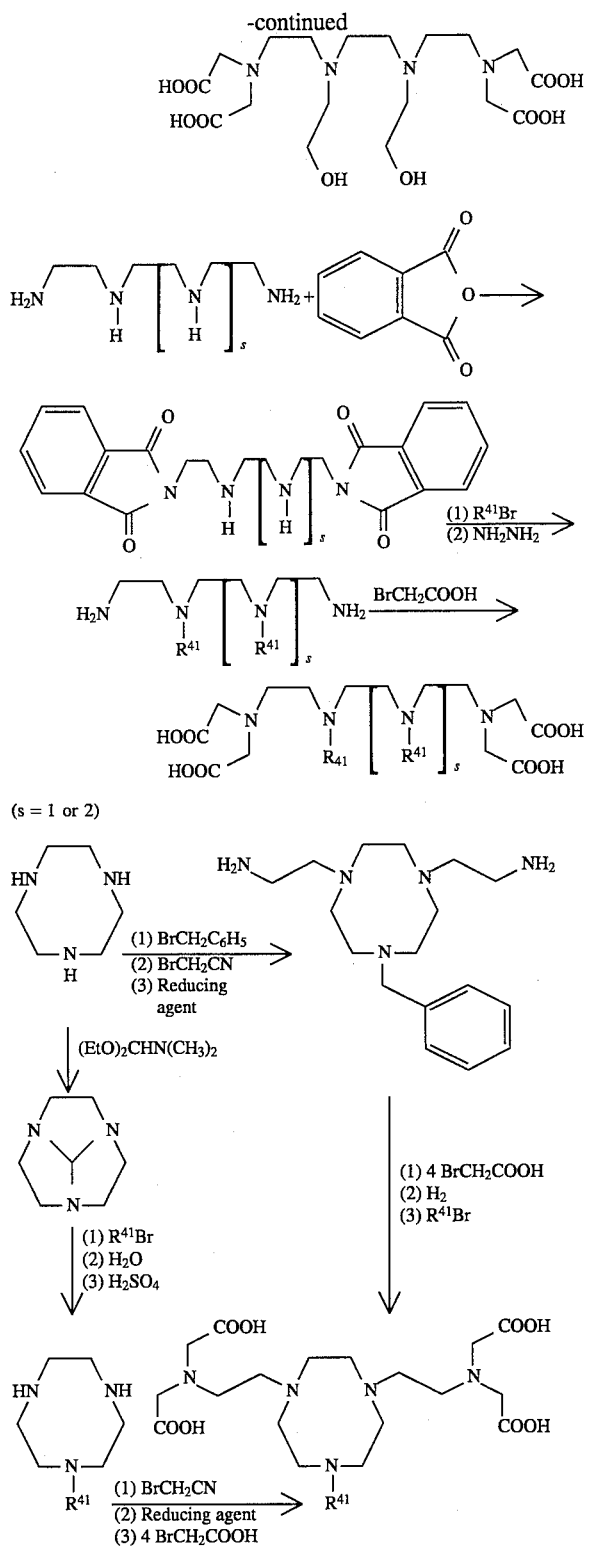

(s = 1 or 2)

or

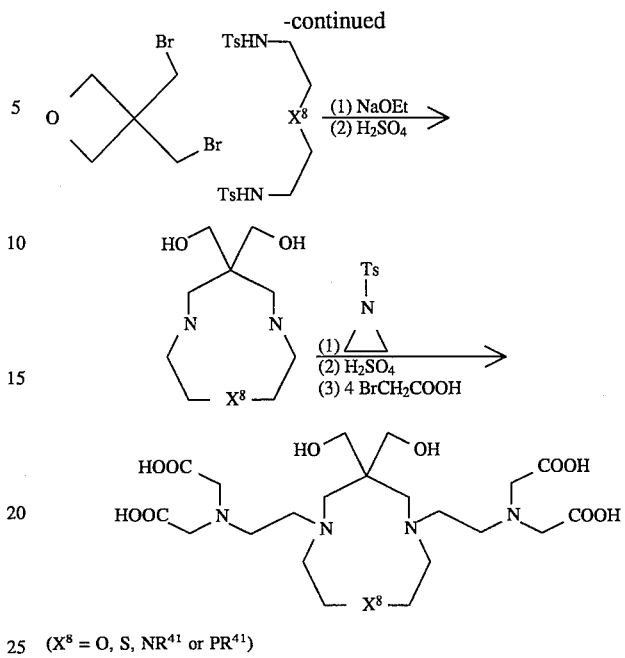

($X^8$ = O, S, $NR^{41}$ or $PR^{41}$)

The multinuclear complexes used according to the invention may be prepared by the methods suggested in the literature or by analogous methods. In particular, novel complexes may be prepared from known complexes by ligand interchange.

Thus, for example for tungsten based multinuclear entities as mentioned above, oxalatotungstate(V) may be used as a starting material and ligand exchange reactions with calcium chelates of APCAs to precipitate out calcium oxalate may be carried out. Chromatographic isolation and purification methods, such as suggested by Ikari (supra) appear particularly suitable.

The preparation of an intermediate oxalate may be avoided by use of other literature known methods, e.g. the electrochemical reduction suggested by Baba et al. Mem. Fac. Tech. Tokyo Metropolitan Univ. 32: 3207 (1982).

Other preparative techniques that deserve particular mention include the oxidation of tungstate complexes with the addition of the desired chelant/complexant as suggested by Chaudhuri (supra) and the reduction of tungstates with reductants and a chelant/complexant (which may have oxidative or reductive properties) as suggested by Lozano et al. in Polyhedron 31: 25–29 (1984).

Further examples of synthetic routes by which the multinuclear complexes used according to the invention may be prepared include:

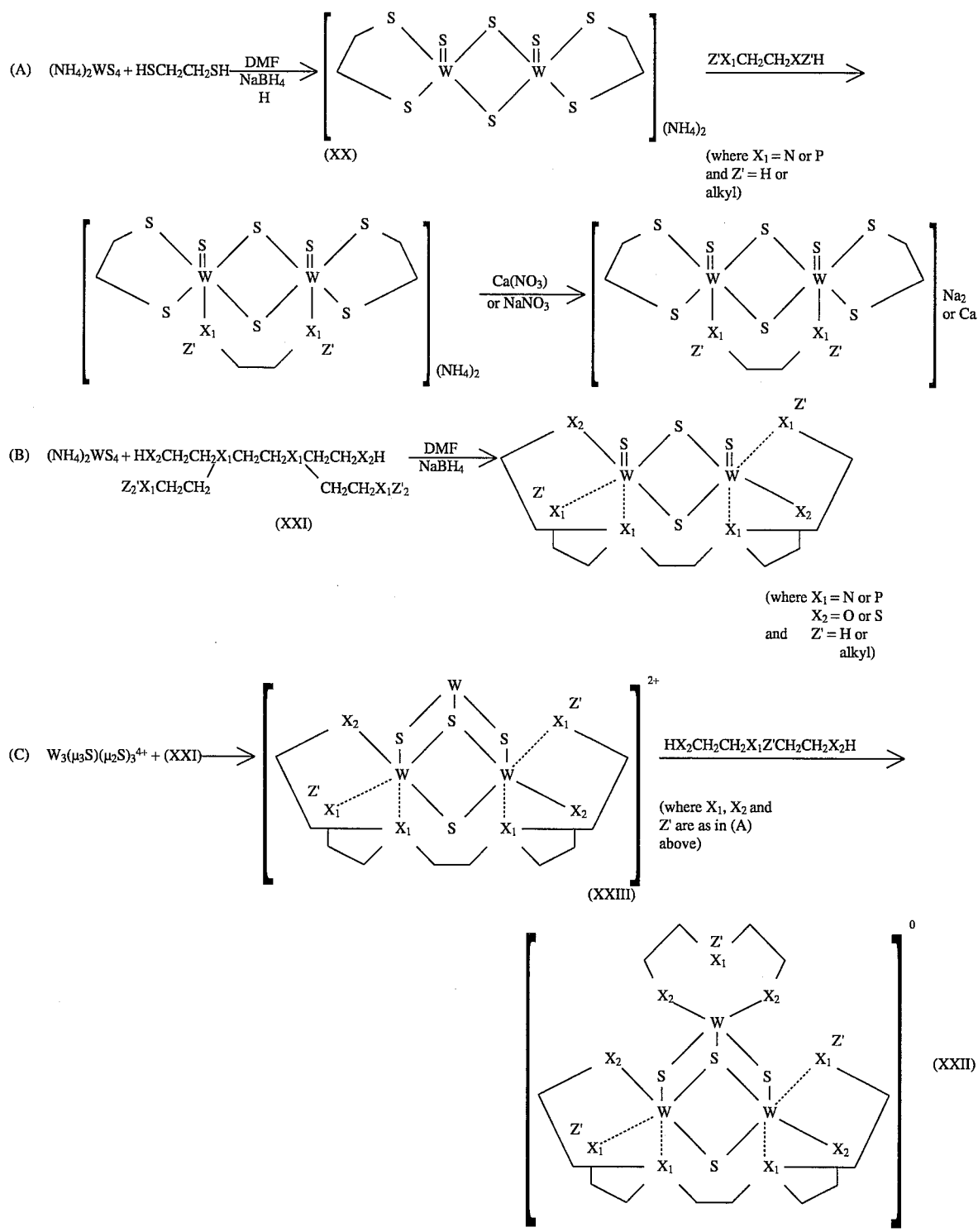

Molybdenum and tungsten trinuclear aqua complexes $[M_3(\mu_3 B)(\mu_2 B)_3(H_2O)_9]^{4+}$ (where M is Mo or W and B is O or S) can be prepared by methods known from the literature. The co-ordinated waters in these complexes can readily be replaced by chelants xvi to xxiii to reduce toxicity. Single or mixed ligand combinations may be used to produce ionic or non-ionic complexes.

The chelated molybdenum and tungsten $M_3$ complexes can also be prepared by reaction of chelants (xvi) to (xxiii) with $[M_3(\mu_3\text{-}S)(\mu_2\text{-}S_2)_3]X_4$ (where X=Cl, Br, I and M=Mo or W) or $[M_3(\mu_3\text{-}S)(\mu_2\text{-}S_2)(S_2)_3]^{2-}$. These latter $M_3$ core complexes are already known from the literature or may be prepared by methods analogous to those known.

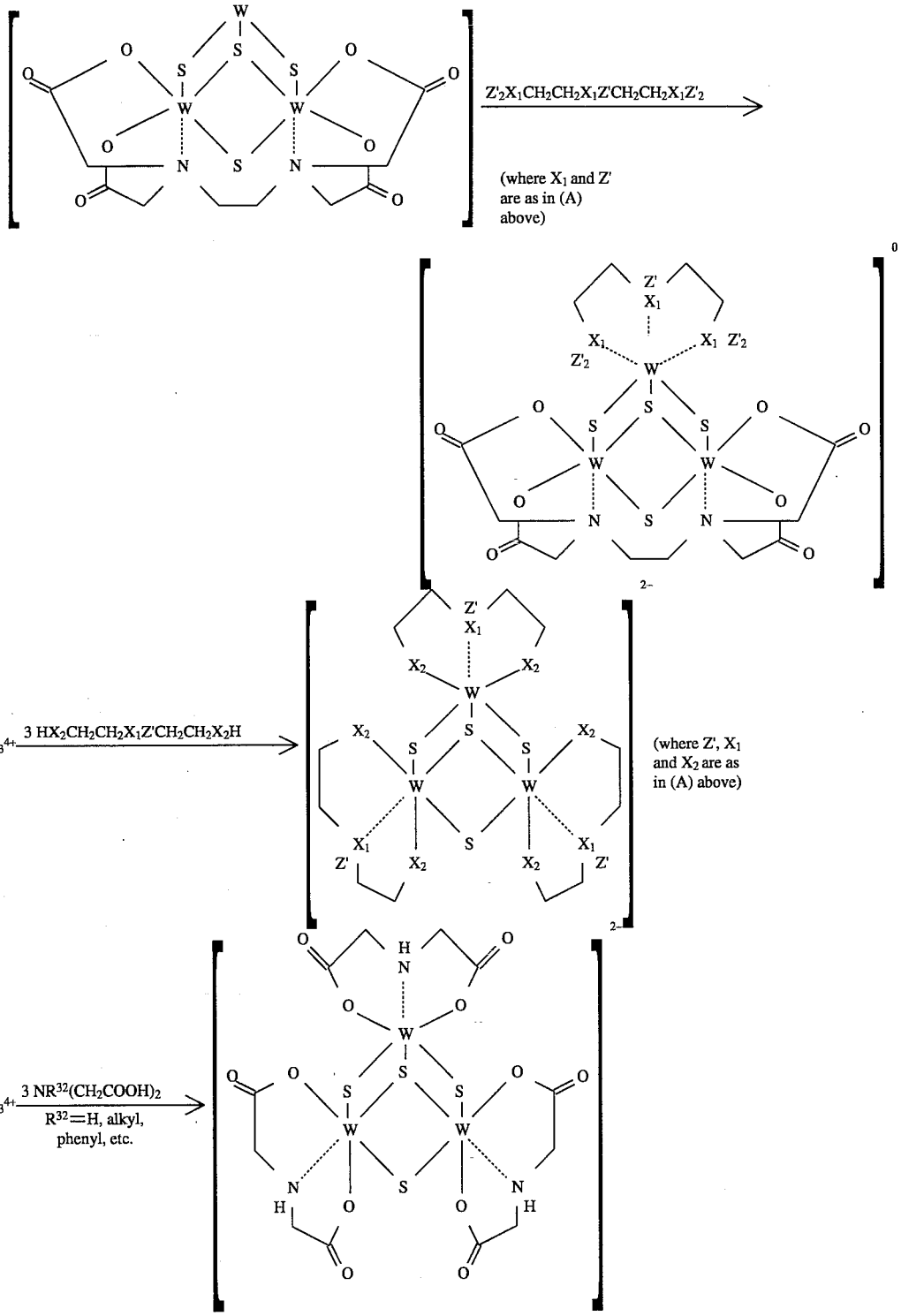

(G) $(W_3(\mu_3S)(\mu_2S)_3^{4+} + [N(COCH_2C(CH_3)_2SH)-(CH_2)_k]_3 \rightarrow$
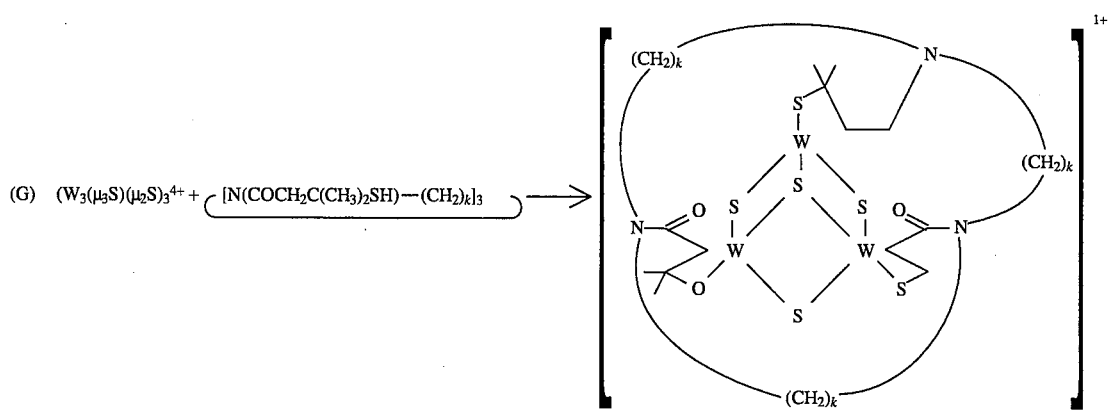
The coordinated water in the tetranuclear aqua complexes may be substituted by ligands such as chelants i to vii to reduce toxicity. Selected examples are shown below.
(H) $[W_4(\mu_3S)_4]^{n+}$ (n = 4 or 5) $\xrightarrow{\text{2 EDTA}}$
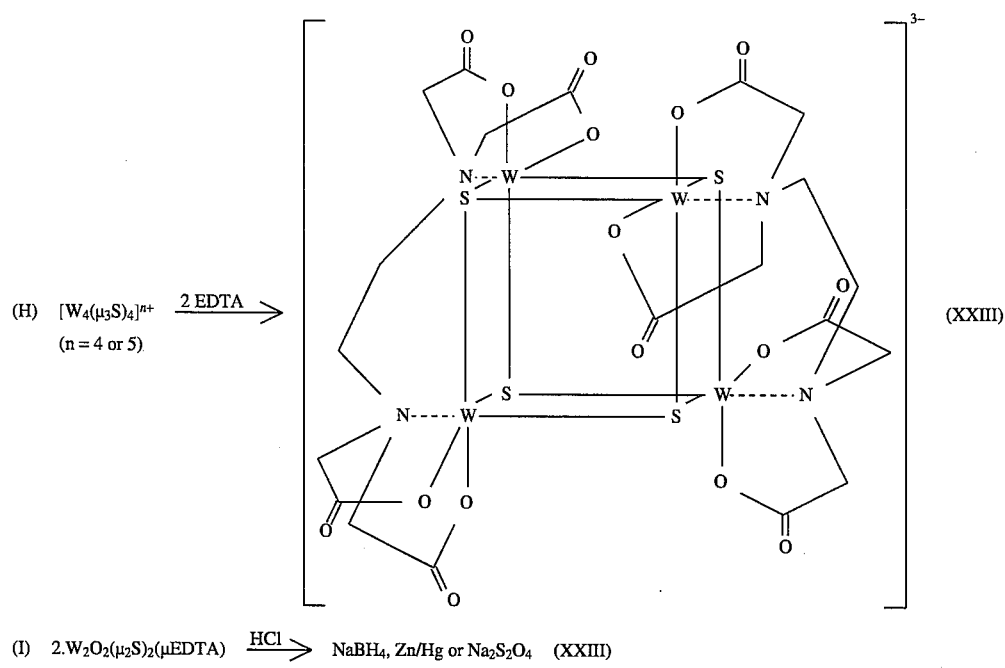
(XXIII)
(I) $2.W_2O_2(\mu_2S)_2(\mu EDTA) \xrightarrow{HCl} NaBH_4, Zn/Hg \text{ or } Na_2S_2O_4$ (XXIII)

(J) $[W_4(\mu_3S)_4]^{n+}$ + (XXI) ⟶

(n = 4 or 5)

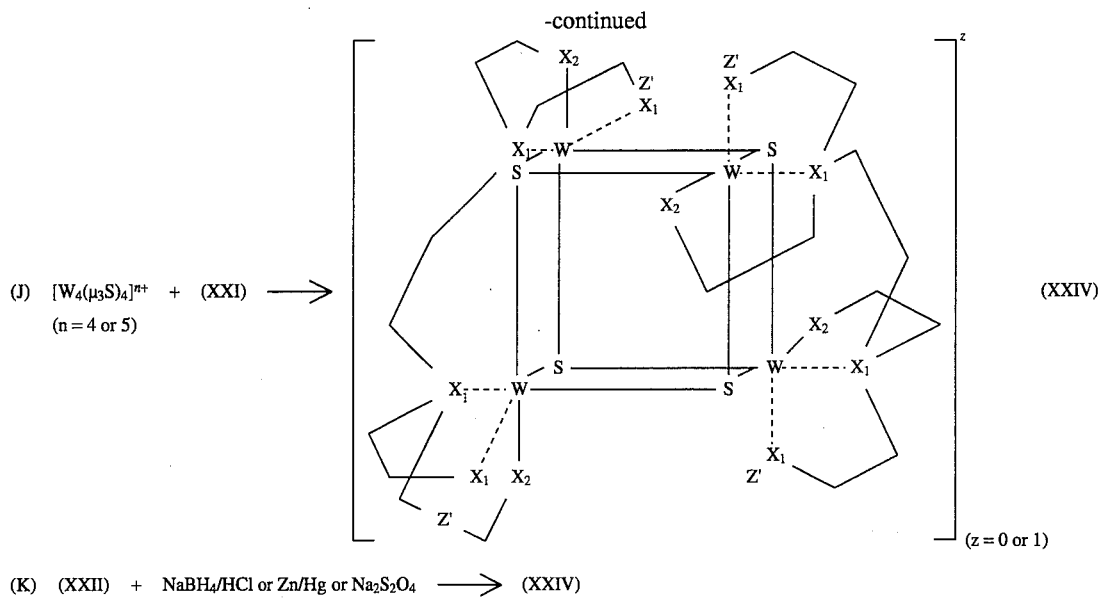

(XXIV)

(z = 0 or 1)

(K) (XXII) + NaBH$_4$/HCl or Zn/Hg or Na$_2$S$_2$O$_4$ ⟶ (XXIV)

(L) $W_4(\mu_3S)_4^{5+}$ + 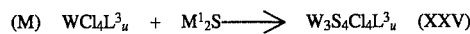 ⟶

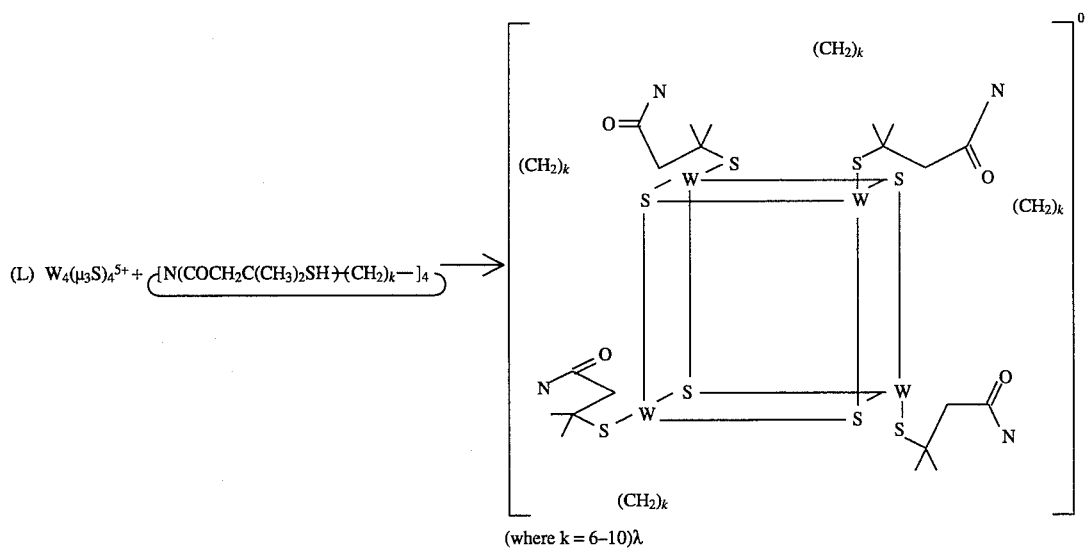

(where k = 6–10)λ

(M) WCl$_4$L$^3_u$ + M$^1_2$S ⟶ W$_3$S$_4$Cl$_4$L$^3_u$ (XXV)

(where L$^3$ is THF, diethylthioether, THT, pyridine, phosphine etc.,

M$^1$ is hydrogen, alkali metal (e.g. Na, Li, K), ammonium, quaternary ammonium, etc, is an integer).

This reaction is conveniently performed in a solvent such as THF, THT, DMF etc. under an inert atmosphere.

The product (XXV) is then treated with water to produce W$_3$S$_4$Cl$_4$(H$_2$O)$_9$ (compound (XXVI)) which can be used to produce larger clusters.

(N) WCl$_4$+Na/Hg+u L$^3$→WCl$_3$L$^3_u$

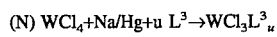

 (XXVII)

The reactions are performed using solvents and an inert atmosphere as discussed under (M) above.

(O) (XXV)+W(CO)$_6$→(XXVII)

The reaction is effected using photolysis in solvents and under an inert atmosphere as discussed under (M) above.

P) 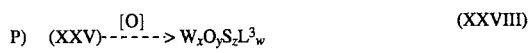 (XXVIII)

(where x, y, z and w are integers)

The oxidizing agent ([o]) is conveniently hydrogen peroxide, OCl$^-$, TBHP, O$_2$, O$_3$ or a peracid. The oxidation is suitably carried out in a solvent such as described under (M) above and can be performed to yield a family of W(VI) mixed sulfur/oxygen clusters.

(Q) 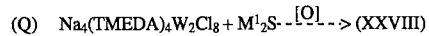

This alternative route to the W(VI) mixed sulphur/oxygen clusters is also conveniently performed using oxidizing agents and solvents as described under (M) and (P) above.

The clusters produced according to processes (M)–(Q) may be reacted to replace $L^3$ ligands by water-soluble chelating agents, e.g. such as those discussed above, to produce more soluble products.

Molybdenum and tungsten based tetranuclear aqua complexes $(M_4(\mu_3B)_4(H_2O)_{12})^{n+}$ (where M=W or Mo, B=S, O, Te or Se and n=4 or 5) can be prepared by various chemical and electrochemical procedures. Tetranuclear tungsten complexes may also be prepared by reduction of binuclear complexes, e.g. using reductants such as $NaBH_4$, $Na_2S_2O_4$, $Zn/H_2$, and Na/Hg amalgam and the compound of formula XXIV, by photo-irradition of tungsten hexacarbonyl and sodium sulphide in methanol, or of a mixture of a trinuclear complex and tungsten hexacarbonyl in methanol or reaction of a trinuclear complex and the W(III) aquo-ion under reducing conditions with heat or photo-irradition.

For use as X-ray or MRI contrast agents, the multinuclear complexes of the lanthanides, of iron and of manganese are particularly attractive. In this regard particular mention may be made of the $Ln_aCu_b$ (where $a \geq 2$ and $b \geq 1$ and Ln is a lanthanide, especially Gd or Dy or La) complexes such as $Ln_4Cu_4$, $Ln_2Cu_4$, $Ln_8Cu_{12}$, $Ln_2Cu_2$ and $Ln_3Cu$ and also of the hexanuclear Fe(III) complexes and Mn(II)/Mn(III) heptanuclear complexes of the types described in the references cited above, e.g. Angew. Chem. Int. Ed. Engl 30:598, 688 and 1139 (1991), Inorg. Chem. 29:1750 (1990) and 31:110 (1992), JACS 113:7940 (1991) and Polyhedron 8:1531 (1989).

For adminstration to human or animal subjects, the multinuclear complexes will conveniently be formulated together with pharmaceutical or veterinary carriers or excipient. The contrast media of the invention may conveniently contain pharmaceutical or veterinary formulation aids, for example stabilizers, antioxidants, osmolality adjusting agents, buffers, pH adjusting agents, colorants, flavours, viscosity adjusting agents and the like. They may be in forms suitable for parenteral or enteral administration, for example, injection or infusion or administration directly into a body cavity having an external voidance duct, for example the gastrointestinal tract, the bladder and the uterus. Thus the media of the invention may be in conventional pharmaceutical adminstration forms such as tablets, coated tablets, capsules, powders, solutions, suspensions, dispersions, syrups, suppositories, emulsions, liposomes, etc; solutions, suspensions and dispersions in physiologically acceptable carrier media, e.g. water for injections, will however generally be preferred. Where the medium is formulated for parenteral administration, the carrier medium incorporating the multinuclear complex is preferably isotonic or somewhat hypertonic. Moreover, media for parenteral administration will preferably contain small quantities, e.g. 0.01 to 10 mole percent relative to the multinuclear complex of free chelants or of weak chelate complexes with physiologically tolerable chelated species (e.g. $Ca^{2+}$); small additions of sodium or calcium salts may also advantageously be made.

For use as X-ray contrast media, the media of the invention should generally have a heavy atom content of 1 millimole/l to 5 mole/l, preferably 0.1 to 2 mole/l Dosages of from 0.05 to 2.0 mmoles/Kg, e.g. 0.5 to 1.5 mmoles/kg will generally be sufficient to provide adequate contrast although dosages of 0.8 to 1.2 mmoles/kg will normally be preferred.

For scintigraphy, dosages of the radioactive species will generally be lower.

Where administration of a particular metal to the body is required, a medium comprising clusters essentially as defined in formula I above and as disclosed in WO-A-91/14460, especially $M_n$ clusters (where M is a therapeutically or contrast effective metal and n is 2 or greater) complexed by a chelating ligand L (such as APCA, PZ etc.), may be administered therapeutically. The medium to be administered will contain a therapeutically required metal which may be the same as or replace an image enhancing metal in the multi-nuclear complexes of the present invention. Preferred therapeutic metals include Sb, Ti, Mo, Pd, W. For therapeutic media, polyoxyanions—especially HPA's (heteropolyoxyanions)—are preferred ligands. In addition, the clusters of the present invention may be used advantageously in bioanalytical applications. Thus, a further aspect of the present invention includes therapeutic and bioanalytical uses of multi-nuclear complexes of formula I.

Thus in summary the present invention provides a particularly effective means by which contrast media efficiency may be enhanced by increasing the relative proportion of molecular volume that is occupied by the contrast enhancing heavy or paramagnetic metal atom. For X-ray contrast media in particular, this also enables higher K-edge value atoms than the iodine of the now conventional X-ray contrast media to be utilized effectively.

The present invention will now be illustrated further by the following non-limiting Examples (all ratios and percentages are by weight and all temperatures are in degrees Celsius unless specified otherwise):

INTERMEDIATE EXAMPLE 1

Preparation of $[W_3(\mu_3\text{-}S)(\mu_2\text{-}S)_3(H_2O)_9]Cl_4$

Method A 25 g of $(NH_4)_2WS_4$ was dissolved in 500 mL of water to give a yellow solution. Aliquots of 2.5 g $NaBH_4$ and 50 mL HCl (concentrated) were added alternatively. 450 mL of HCl (concentrated) was then added to the mixture. The material was heated to 100° C. in an oil bath. 3.2 g of Sn was added in several aliquots and the mixture was heated for six hours. The material was cooled and filtered through a pyrex fritted funnel and the resulting brown solution was heated to 100° C. in an oil bath. $O_2$ was bubbled through the solution for about 4 hours until the solution turned purple and the solution was allowed to stand for several days. The solution volume was reduced to 200 mL, loaded onto a G-15 Sephadex column and eluted with 2N HCl. The fourth band (dark purple) was collected. The solution was evaporated to dryness under high vacuum at 36°–40° C. to give the title compound as a dark solid. The yield was 4.80 g (19.2%). UV/vis spectroscopy shows $\lambda$ max at 310 nm and 570 nm.

Method B

The title compound was prepared by a slightly modified version of the procedure described in JACS 108:2757–2758 (1986).

3 g of $(NH_4)_2WS_4$ (8.62 mmol) was dissolved in 75 ml of water to give a yellow solution. 3 g of $NaBH_4$ and 30 ml of concentrated HCl were added alternatively to the tungsten solution. Upon this addition, an immediate color change from yellow to dark brown was observed. The resulting brown suspension was heated at 100° C. for 2 hours. After cooling the mixture, it was filtered to remove a dark brown solid and to obtain a brown filtrate. The brown solution was loaded on a Sephadex G-15 column, which resulted in a brown band on top of the column. After a 5-day air oxidation of the brown band, it was eluted with 2M HCl solution. The second purple fraction ($\lambda$ max=570 nm and 320 nm) was collected and evaporated to dryness under high vacuum at 36°–40° C., which gave dark solid. The product was washed with acetone and dried in the air. The yield was 0.506 g (0.62 mmol, 22%).

The mass spectral data in dithiothrietol(DTT)/dithioerythrietol matrix gives a molecular ion at 1139 equivalent to the mass of $[W_3S_4(DTT)_3]+2H^+$.

The elemental analysis indicated that the product was $W_3S_4(H_2O)_9Cl_4$ and contained 2.4% HCl and 3.9% $H_2O$.

Calculated: W(52.53%), S(12.22%), Cl(15.86%). Found: W(52.46%), S(12.24%), Cl(15.96%).

INTERMEDIATE EXAMPLE 2

Preparation of $W_3(\mu_3\text{-S})(\mu_2\text{-O})_3(H_2O)_9Cl_4$

The title compound was prepared by a slightly modified version of the procedure described in Cotton, F. A., et. al., Polyhedron 5; 907 (1986). 1.0 g $W(CO)_6$ was refluxed with 0.8 g anhydrous $Na_2S$ in 100 mL of acetate anhydride for 12 hours under $N_2$. The product was dissolved in 0.3 M HCl. The solution was loaded onto a AG50W-X8 cation-exchange column. Elution with 0.3M HCl yielded an orange band (1st band), peak at 458 nm, identified as $W_3O_3S(H_2O)_9CL_4$ ($\epsilon$ 349 $M^{-1}cm^{-1}$). The isolated band was purified on a second cation-exchange column and evaporated to dryness under high vacuum at 45° C., which gave an orange solid. The yield was 0.2 g.

INTERMEDIATE EXAMPLE 3

Preparation of $[W_3(\mu_3\text{-S})(\mu_2\text{-S})_2(\mu_2\text{-O})]Cl_4(H_2O)_9$ The title compound was prepared according to the procedure of Sykes, et. al., Inorg. Chem 30: 5043–5046 (1991). Air-free solutions of $(NH_4)_2WS_4$ in $H_2O$ and $K_3[W_2Cl_9]$ in 3M HCl were mixed. The solution was heated to 90° C. for 2 hours, cooled and filtered. The solution was loaded onto a Dowex 50W-X2 cation-exchange column. The column was washed first with 0.5M HCl and then 1.0 M HCl to obtain three bands. Elution with 2M HCl yielded a purple-red band (2nd band), peak at 540 nm, identified as $W_3OS_3(H_2O)_9Cl_4$ ($\epsilon$ 408 $M^{-1}cm^{-1}$). The isolated band was purified on a second cation-exchange column.

The reagent $K_3[W_2Cl_9]$ can be prepared as described by Shibahara et al., Inorg. Chim Acta 127: L39 (1987).

INTERMEDIATE EXAMPLE 4

Preparation of $[W_3(\mu_3\text{-S})(\mu_2\text{-S})(\mu_2\text{-O})_2]Cl_4(H_2O)_9$ The title compound was prepared according to the procedure of Sykes et. al., Inorg. Chem 30: 5043–5046 (1991). Air-free solutions of $(NH_4)_2WS_4$ in $H_2O$ and $K_3[W_2Cl_9]$ in 3M HCl were mixed. The solution was heated to 90° C. for 2 hours, cooled and filtered. The solution was loaded onto a Dowex 50W-X2 cation-exchange column. The column was washed first with 0.5M HCl and then 1.0 M HCl to obtain three bands. Elution with 2M HCl yielded a red band (1st band), peak at 506 nm, identified as $W_3O_2S_2(H_2O)_8Cl_4$ ($\epsilon$ 381 $M^{-1}cm^{-1}$). The isolated band was purified on a second cation-exchange column.

INTERMEDIATE EXAMPLE 5

Preparation of $[W_3(\mu_3\text{-O})(\mu\text{-O})_3]Cl_4(H_2O)_9$

The title compound is prepared according to the procedure of Sykes et. al., Inorg. Chem 27: 3626–3629 (1988). Air-free solution of $K_2[WCl_6]$ in 2M HPTS is heated to 90° C. for 2.5 hours, cooled and filtered. The solution is loaded onto a Dowex 50W-X2 cation-exchange column. The column is washed first with 1.0M HPTS and then 2.0M HPTS. Elution with 4M HPTS yields a red band, peak at 455 nm, identified as $W_3O_4(H_2O)_9Cl_4$ ($\epsilon$ 375 $M^{-1}cm^{-1}$). The isolated band is purified on a second cation-exchange column.

The reagent $K_2[WCl_6]$ can be prepared as described by Kennedy, et. al., J. Chem. Soc. (1963) 3392.

INTERMEDIATE EXAMPLE 6

Preparation of TTHA-BDHA Ligand a) Triethylenetetramine hexaceticacid (5.0 g, 10.1 mmol) and acetic anhydride (9.55 mL, 101 mmol) were dissolved in dry pyridine and heated to 65° C. with stirring for 18 hours. To the resulting dark brown slurry was added diethyl ether, the solution was filtered, washed twice with acetonitrile, and the solid was dried in vacuo to give 3.43 g of TTHA-bis-anhydride as a tan powder (74%). $^1H$ NMR ($d^6$-DMSO) 2.61 (t, 4H), 2.79 (m, 9H), 3.24 (s, 4H), 3.70 (s, 8H).

b) Diethanolamine (4.61 mL, 48.2 mmol) was dissolved in water, and chilled to 5° C. To this solution was added TTHA-bis-anhydride (3.68 g, 8.03 mmol) in portions. The solution was allowed to warm to ambient temperature, and stirred for 24 hours. The pH of the resulting solution was adjusted to about 9 and it was purified by ion exchange chromatography. Fractions containing the desired product were collected, decolorized with carbon black, evaporated and dried in vacuo at 50° C. for 48 hours to give the title compound N,N''''-di(N,N-bis-2-hydroxyethylaminocarbonylmethyl)triethylenetetramine-N,N',N'',N''' -tetraacetic acid) as a pale yellow solid (2.15 g, 40%). $^1H$ NMR ($D_2O$) 3.05 (s, 4H), 3.10 (s, 4H), 3.28 (m, 12H), 3.46 (s, 12H), 3.61 (s, 4H), 4.14 (s, 4H).

$^{13}C$ NMR ($D_2O$) 48.2; 49.8; 51.0; 51.7; 52.4; 55.7; 56.5; 57.7; 58.5; 58.8; 168.6; 170.3; 172.4.

FAB-MS: M+H 669.5.

INTERMEDIATE EXAMPLE 7

Preparation of N',N''-di[bis(hydroxyethyl)aminoethyl]⁻ N,N,N'''N'''-tetraacetic acid-triethylenetetramine a) Triethylenetetramine (7.85 mL, 80.5 mmol) was dissolved in chloroform and chilled to −5° C. To this was added slowly and with stirring a solution of ethyltrifluoroacetate (17 mL, 15.6 mmol) in chloroform. When the addition was complete, the solution was allowed to warm to ambient temperature and stirred for 18 hours. The resulting slurry was chilled again to −5° C., filtered, the cake was washed with cold chloroform and dried in vacuo to give 14.2 g of N,N''''-ditrifluoroacetyl triethylenetetramine as a white powder (54%).

b) A solution of N,N''''-ditrifluoroacetyl triethylenetetramine (1 equivalent), N-2-bromoethyl-N,N-di(t-butylacetyl)amine (2.5 equivalents) and diisopropylethylamine (5 equivalents) in acetonitrile is stirred for 24 hours at reflux. The solution evaporated to dryness, dissolved in chloroform, and washed twice with water, once with saturated sodium chloride solution, dried over $MgSO_4$, and purified on a silica gel column to give N,N,N''',N'''-tetra(t-butyloxycarbonylmethyl)-N',N'' -ditrifluoroacetylaminomethyl-triethylenetetramine.

c) N,N,N''',N''''-tetra(t-butyloxycarbonylmethyl)-N',N'' -ditrifluoroacetylaminomethyl-triethylenetetramine is dissolved in a methanol/water solution of potassium carbonate (20 equivalents) and heated to 60° C. with stirring for 6 hours. The solution is evaporated to dryness and extracted several times with chloroform. The extracts are evaporated to give N,N,N''',N'''' -tetra(t-butyloxycarbonylmethyl)-N', N''-di(2-aminoethyl)-triethylenetetramine.

d) N,N,N''',N''''-tetra(t-butyloxycarbonylmethyl)-N',N'' -di(2-aminoethyl)-triethylenetetramine is dissolved in acetonitrile with an excess of potassium carbonate, and a solution of bromoethanol (3 equivalents) in acetonitrile is added dropwise with stirring; the solution is then heated to reflux for 18 hours. The reaction mixture is then filtered and the filtrate evaporated to dryness to give N,N,N''',N'''' -tetra(t-butyloxycarbonylmethyl)-N',N''-di(N,N-bis(2-hydroxyethyl)-2 -aminoethyl)-triethylenetetramine.

e) N,N,N''',N''''-tetra(t-butyloxycarbonylmethyl)-N',N'' -di(N,N-bis(2-hydroxyethyl)-2-aminoethyl)-triethylenetetramine is dissolved in methylene chloride and trifluoroacetic acid is added dropwise. The solution is stirred for one hour and evaporated to dryness, and the hydrloysis is repeated three more times, to give the title compound.

INTERMEDIATE EXAMPLE 8

Preparation of N,N'-di[bis(carboxymethyl)aminoethyl]N'' -hydroxyethyl-TACN a) To a chilled solution of triazacyclononane (TACN) (100 mg, 0.74 mmol) in acetonitrile was added with stirring triphenylmethyl chloride (216 mg, 0.774 mmol) in acetonitrile. The solution was allowed to warm to room temperature and stirred for 18 hours. The resulting slurry was filtered, the cake was washed twice with acetonitrile, and dried in vacuo to give 151 mg of 1-triphenylmethyl-1,4,7-triazacyclononane (48%).

b) A solution of 1-triphenylmethyl-1,4,7-triazacyclononane (1 mmol), N-2-bromoethyl-N,N-di(t-butylacetyl)-amine (2.5 mmol) and diisopropylethylamine (5 mmol) in chloroform is stirred for 24 hours at reflux. The solution is washed twice with water, once with saturated sodium chloride solution, dried over MgSO$_4$, and purified on a silica gel column to give N,N-di(N,N-di-t-butylacetyl)aminoethyl-N'' -(triphenyl)methylTACN.

c) The tetraester, N,N-di(N,N-di-t-butylacetyl)aminoethyl-N'' -(triphenyl)methylTACN is dissolved in methylene chloride and trifluoroacetic acid is added dropwise. The solution is stirred for one hour and evaporated to dryness, and the hydrolysis is repeated three more times, to give N,N'-di(N,N-di-acetyl)aminoethyl TACN.

d) N,N'-di(N,N-di-acetyl)aminoethyl TACN is dissolved in aqueous NaOH at pH 11 and bromoethanol is added dropwise with stirring. The solution is then heated to 40° C. for 18 hours and the resulting solution is passed through an ion exchange column to give the title compound.

INTERMEDIATE EXAMPLE 9

Preparation of tris[(dicarboxymethyl)aminoethyl] TACN

TACN (0.129 g, 0.001 mol) in water containing a trace of sodium iodide was treated with N-(2-chloroethyl)iminodiacetic acid hydrochloride (0.765 g, 0.0033 mol) at 40° C. and pH 11.5–12 (NaOH). After 3 hours, the solution was passed through a column of Amberlite IR 120 ion exchange resin (acid form) and evaporated to dryness. The solid residue was recrystallized from methanol/isopropanol to yield tris[(dicarboxymethyl)-aminoethyl]TACN as a white solid, whose identity was confirmed by FAB-MS,MH$^+$=607.

The title compound was also prepared by the reaction of TACN with the dimethyl ester of N-(2-chloroethyl)iminodiacetic acid in the presence of excess K$_2$CO$_3$ in refluxing acetonitrile for 24 hours. This yielded the hexamethyl ester, which was converted to the free acid by refluxing in 3N hydrochloric acid for three hours, followed by evaporation to dryness.

INTERMEDIATE EXAMPLE 10

Preparation of N',N''-bis(carboxymethyl)triethylene tetramine a) A solution of 15 g (0.102 mol) of triethylene tetramine and 150 mL of chloroform were stirred in a round bottom flask at 0° C. A solution of 28.4 g (0.200 mol) of ethyl trifluoroacetate in 25 mL of chloroform was added dropwise and the reaction allowed to warm to ambient temperature. A white precipitate was observed after approximately 1 hour. After 20 hours, the precipitate was filtered off and rinsed with ethyl ether to afford 16.5 g(48%) of white solid. $^1$H NMR (D$_2$O) δ 2.64 (s, 2H), 2.72 (m, 4H), 3.38 (m, 4H).

b) 6.45 g (0.0191 mol) of N',N'''-bis-trifluoroacetyl-triethylene tetramine and 7.40 g (0.0573 mol) of di-isopropylethyl amine were dissolved in 75 mL of acetonitrile and 25 mL of chloroform. 7.44 g (0.0381 mol) of t-butyl bromoacetate in 20 mL of acetonitrile were added dropwise and the reaction was heated to 60° C. After 72 hours, the solvent was stripped off and the resulting yellow solid taken up in 40 mL of chloroform and extracted with H$_2$O (3×20 mL), dried over MgSO$_4$ and concentrated to a yellow oil. The oil was stirred in 50 mL of petroleum ether which afforded 1.14 g (70%) of white solid which was filtered off. $^1$H NMR (CDCl$_3$) δ 1.43 (s, 18H), 2.67 (s, 4H), 2.73 (m, 4H), 3.24 (s, 4H), 3.33 (m, 4H).

c) 1.14 g (0.0020 mol) of N,N'''-bis-trifluoroacetyl-N',N'' -bis(t-butyl acetate) triethylene tetramine were dissolved in 80 mL of methanol and 10 mL of water. 2.22 g (0.0161 mol) of potassium carbonate were added and the reaction was heated to 60° C. After 2 hours, the solvent was stripped off to a white solid, The solid was stirred in 40 mL of methanol and the solid filtered off. This step results in hydrolysis of the TFA groups and cleavage of the t-butyl protecting groups. The mother liquor was concentrated to yield the title compound and a yellow oil. Further purification of the oil was achieved by ion-exchange chromatography utilizing BioRad AG1-X8 anion exchange resin. $^1$H NMR (D$_2$O) δ 2.5 (s, 4H), 2.59 (m, 4H), 3.0 (s, 4H), 3.15 (m, 4H).

INTERMEDIATE EXAMPLE 11

Preparation of N,N,N''',N''''-tetra(carboxymethyl)-N',N'' -bis(hydroxyethyl) triethylene tetramine a) 2.0 g (0.0135 mol) of bis-hydroxyethyl ethylene diamine were dissolved in 50 mL of methanol. 5.8 g (0.027 mol) of BOC-O-BOC in 5 mL of methanol were added dropwise and the reaction stirred at 25° C. for 20 hours. The solvent was stripped off to afford a white solid. To achieve further purification, the solid was washed with ethyl ether to yield 4.0 g (85%) of the desired product N',N''-bis-butoxycarbonyl-N',N"-bis-hydroxyethyl ethylene diamine. $^1$H NMR δ 1.48 (s, 18H), 3.5 (m, 8H), 3.7 (m, 4H).

b) 27.5 g (0.161 mol) of benzyl bromide and 30 mL of THF were stirred in a round bottom flask. 0.7 g (0.0203 mol) of sodium hydride was added which produced vigorous bubbling and the formation of a white solid. 4.0 g (0.0115 mol) of N',N"-bis-butoxycarbonyl-N',N"-bis-hydroxyethyl ethylene diamine were added and the reaction allowed to stir at 25° C. Further precipitation of a white solid was observed. After 24 hours, the reaction was stopped by the addition of 150 mL of a 1:1 mixture of methylene chloride and water. The organic layer was separated and washed with water (4×50 mL), dried over $MgSO_4$ and concentrated to yield N',N"-bis-butoxycarbonyl-N',N" -bis-ethoxybenzyl ethylene diamine as a yellow oil. The oil was distilled under vacuum to remove excess benzyl bromide and then placed under vacuum. $^1$H NMR δ 1.4 (s, 18H), 3.5 (m, 12H), 4.44 (s, 4H), 7.3 (s, 10H).

c) N',N"-bis-butoxycarbonyl-N',N"-bis-ethoxybenzyl ethylene diamine was used directly after the distillation without any further purification. The oil was dissolved in 50 mL of methylene chloride and stirred at 25° C. 50 mL of trifluoroacetic acid were added dropwise and the reaction allowed to stir for 24 hours. The solvent was then stripped off and the resulting brown oil chased with small amounts of methylene chloride. The oil, N',N"-bis-ethoxybenzyl ethylene diamine, was solidified by placing under vacuum for several hours. $^1$H NMR δ 3.17 (m, 4H), 3.5 (s, 4H), 3.64 (m, 4H), 4.47 (s, 4H), 7.3 (s, 10H).

d) 12.0 g (0.0586 mol) of bromoethyl amine hydrobromide and 34.1 g (0.264 mol) of diisopropylethyl amine were dissolved in 200 mL of acetonitrile. 24.0 g (0.123 mol) of t-butyl bromoacetate in 25 mL of acetonitrile were added dropwise and the reaction was stirred at 60° C. After 48 hours, the reaction was stopped and the solvent was stripped off by rotary evaporation. The resulting solid was taken up in 50 mL of chloroform and extracted with $H_2O$ (3×40 mL), dried over $MgSO_4$ and concentrated to a brown oil, N,N-di-(t-butyl acetate) bromoethyl amine. Further purification was achieved by flash chomatography eluting with 10% methanol/chloroform ($R_f$=0.95). The column yielded 9.5 g (48%) of pure product. $^1$H NMR δ 1.45 (s, 18H), 3.13 (m, 2H), 3.47 (m, 6H).

e) 500 mg (0.0015 mol) of N,N"-bis-ethoxybenzyl ethylene diamine and 776 mg (0.0060 mol) of di-isopropylethyl amine were combined in 30 mL of acetonitrile and stirred at 25° C. 1.07 g (0.0030 mol) of N,N-di-(t-butyl acetate) bromoethylamine in 5 mL of acetonitrile was added dropwise and the reaction was heated to 60° C. and a catalytic amount (10% w/w) of sodium iodide was added. After 24 hours the solvent was stripped off by rotary evaporation which gave a yellow solid. The solid was dissolved in 30 mL of chloroform and extracted with water (6×20 mLs), dried over $MgSO_4$ and concentrated to a yellow oil, $N^1,N^1,N^4,N^4$-tetra-(t-butyl acetate)-$N^2,N^3$-bis-ethoxybenzyl triethylene tetramine.

f) The oil obtained in step (e) was used without any further purification. The oil was dissolved in 20 mL of methylene chloride and 20 mL of trifluoroacetic acid were added dropwise. The reaction was stirred for 24 hours at 25° C. The solvent was then stripped off and the resulting oil taken up in 30 mL of methanol. A catalytic amount of palladium was added and the reaction allowed to stir at 25° C. for 24 hours under a hydrogen atmosphere. The reaction mixture was then filtered through charcoal to remove the catalyst and concentrated to yield the title compound as a yellow solid.

The title compound was further purified by ion-exchange chromatography.

The ligands of Intermediate Examples 6 to 11 may be used in the subsequent Examples in place of the ligands actually specified, eg. DTPA, EGTA, EDTA, etc.

EXAMPLE 1

Bis(μ-oxo)(μ-N,N'-propylenediaminetetraacetato)-bis(oxotungstate(V)), barium salt
$Ba[W_2O_2(\mu_2O)_2(\mu_2PDTA)]$ The potassium salt (1.61 g, 1 mmol) of the oxalato complex of tungsten(V) (prepared according to Baba et al., Mem. Fac. Tech. Tokyo Metropolitan Univ. 32: 3207–3220 (1982)) and 1,2-diaminopropane-N,N,N',N'-tetraacetic acid (0.612 g, 2 mmol) were dissolved under nitrogen in a mixture of 50 ml oxygen-free water and sodium acetate-solution (1M, 8 ml) and heated to 100° C. Calcium acetate-solution (1M, 10 ml) was added with stirring and the mixture allowed to cool. After filtering off the precipitate, a barium acetate-solution (1M, 2 ml) was added, the solution was filtered and the title compound was precipitated by dropwise addition of ethanol. It was collected on a filter, washed with 50% aqueous methanol and dried in vacuo at 40° C.

Yield: 0.413 g (43%) of the pentahydrate.

EXAMPLE 2

Bis(μ-oxo)(μ-N,N'-propylenediaminetetraacetato)-bis(oxotungstate(V)), disodium salt
$Na_2[W_2O_2(\mu_2O)_2(\mu_2PDTA)]$ Method A:

1 g of 1,2-diaminopropane-N,N,N'N'-tetraacetic acid ($PDTAH_4$) and 1.02 g of sodium acetate were dissolved in 35 ml of hot water giving a clear colorless solution. 1 g of $Na_3[WO_2(C_2O_4)_2].3H_2O$ (prepared according to the procedure of Soares et. al., J. C. S. Dalton, 1101–1104 (1980)), were directly added to the PDTA solution. The resulting orange solution was boiled on a hot plate for 10 minutes to complete the substitution reaction of the coordinated oxalate with PDTA. 2 g of $CaCl_2.2H_2O$ solution in 10 ml of hot water was then added to the orange tungsten solution to precipitate $CaC_2O_4$. After removing the white $CaC_2O_4$ solid by filtration, the orange filtrate was treated with 1.5 g of $BaCl_2.2H_2O$ to obtain $Ba[W_2O_2(\mu_2-O)_2(PDTA)]$. The resulting orange solution was concentrated to 25 ml under reduced pressure to precipitate the excess salts. After the salt was removed by filtration, the orange filtrate was placed on a sephadex G-15 column. The orange eluant with water was treated with $Na_2SO_4$ to convert the barium complex into the sodium one. The insoluble $BaSO_4$ was filtered off and the orange filtrate was reduced to a small volume, 15 ml. The concentrated orange filtrate was mixed with ethanol to precipitate the product. The orange product was collected by filtration, washed with acetone, and dried in the air. The yield was 0.63 g. MS spectral data showed a molecular ion at 767.0, equivalent to the mass of $Na_2[W_2O_2(\mu_2O)_2(\mu_2O)_2(\mu_2PDTA)]+H^+$.

Method B:

The title compound is prepared by dissolving the barium salt of Example 1 in warm water. After addition of a stoichiometric amount of a 1M sodium sulfate solution the mixture is allowed to cool, filtered and the filtrate concentrated to dryness.

EXAMPLE 3

[N(C$_2$H$_5$)$_4$]$_2$[W$_2$S$_2$($\mu_2$-S)$_2$(EDT)$_2$]

This compound was prepared according to a literature procedure. (Inorg. Chem. 23: 4265–4269 (1984)). 0.81 g (2.3 mmol) of (NH$_4$)$_2$WS$_4$ was added to 25 ml of N$_2$-saturated DMF. The resulting mixture was a greenish-yellow suspension. After adding 0.3 ml (3.6 mmol) of 1,2-ethanedithiol (EDT), a bright yellow color formed. The reaction mixture was heated under a N$_2$ flow at 120° C. in an oil bath for 2 hours. After several minutes of heating, the solution became red-orange. At the end of the reaction period, a brownish red suspension was noted, 0.63 g of N(C$_2$H$_5$)$_4$Cl was then added to the cooled suspension at ambient temperature. 20 ml of diethyl ether was added to precipitate the product. Brownish red crystals were recovered by filtration and washed with methanol and then with ether. The addition of more ether (150 ml) to the red-orange filtrate gave more product. All the fractions were then combined and recrystallized once from methanol. The total yield of the product was 0.75 g (1.6 mmol, 69% from (NH$_4$)$_2$[WS$_4$]).

The mass spectral data of this product showed a molecular ion at 681 corresponding to W$_2$S$_4$(EDT)$_2$+H$^+$.

EXAMPLE 4

Preparation of the disodium salt of the W$_3$($\mu_3$-S)($\mu_2$-S)$_3$ complex of triethylenetetraamine-N,N,N',N'',N''',N'''-hexaacetic acid: Na$_2$[W$_3$($\mu_3$-S)($\mu_2$-S)$_3$ (TTHA)]

Method A:

22.70 g of W$_3$($\mu_3$-S)($\mu_2$-S)$_3$(H$_2$O)$_9$Cl$_4$ (Intermediate Example 1) were dissolved in 1000 mL of DMF, forming a dark green solution. 11.77 g of TTHA, dissolved in 1300 mL of DMF were mixed with the tungsten solution. The mixture was refluxed for 5–6 hours until a purple suspension was obtained. After cooling the suspension, the grayish purple solid was collected by filtration and washed with isopropanol and acetone. The solid material was dried at 50° C. in vacuo. The product was the dimethylammonium salt of W$_3$($\mu_3$-S)($\mu_2$-S)$_3$(TTHA). The yield was 25.46 g. Positive ion FAB-MS spectral data showed a molecular ion at 1169, corresponding to the mass of W$_3$($\mu_3$-S)($\mu_2$-S)$_3$(TTHA)+H$^+$.

The dimethylammonium salt of W$_3$($\mu_3$-S)($\mu_2$-S)$_3$(TTHA) was dissolved in a minimum amount of water and loaded onto a column containing BioRad AG50W-X8 resin in the proton form. The dimethyl ammonium cation remains on the column and the product is eluted from the column with water as H$_2$[W$_3$($\mu_3$-S)($\mu_2$-S)$_3$(TTHA)]. The purple effluent is reduced in volume by rotary evaporation and carefully neutralized with 1N NaOH. The purple solution at pH 7 is loaded onto a column containing Sephadex G-15 resin. The second band containing Na$_2$[W$_3$($\mu_3$-S)($\mu_2$-S)$_3$(TTHA)] is eluted with water. The yield was 7.3 g. Positive ion FAB-MS spectral data showed a molecular ion at 1216, corresponding to the mass of Na$_2$[W$_3$($\mu_3$-S)($\mu_2$-S)$_3$(TTHA)+H$^+$. HPLC chromatography indicates a single tungsten containing peak (monitored at 570 nm).

Method B:

2.845 g of W$_3$($\mu_3$-S)($\mu_2$-S)$_3$(H$_2$O)$_9$Cl$_4$ (Intermediate Example 1) were dissolved in 200 ml of DMF, giving a dark green solution. 1.682 g of TTHA, dissolved in 500 ml of DMF, were mixed with the tungsten solution. The mixture was refluxed (3–4 hours) until a purple suspension was obtained. After cooling the suspension, the grayish purple solid was collected by filtration, washed with acetone, and dried in the air. The product was the dimethylammonium salt of W$_3$($\mu_3$-S)($\mu_2$-S)$_3$(TTHA). The yield was 3.021 g. MS spectral data showed a molecular ion at 1168.6, corresponding to the mass of W$_3$($\mu_3$-S)($\mu_2$-S)$_3$(TTHA)+H$^+$.

The sodium salt of the W$_3$($\mu_3$-S)($\mu_2$-S)$_3$ complex of triethylenetetraamine-N,N,N',N'',N''',N''''-hexaacetic acid, Na$_2$[W$_3$($\mu_3$-S)($\mu_2$-S)$_3$(TTHA)], was obtained quantitatively by the following procedure: The dimethylammonium salt of the complex was dissolved in the minimum amount of water and the pH of the solution was adjusted to 7.0 using NaOH solution. The product was then precipitated with isopropanol in the presence of sodium chloride or sodium acetate, washed with methanol, and dried in vacuo at 50° C. The elemental analysis indicted that the product was Na$_2$[W$_3$($\mu_3$-S)($\mu_2$-S)$_3$(TTHA)].H$_2$O.

Calculated: C (17.53%), N (4.54%), Na (3.73%) Found: C (17.58%), N (4.57%), Na (3.78%)

EXAMPLE 5

Preparation of a Solution Containing the Disodium Salt of [W$_3$($\mu_3$-S)($\mu_2$-S)$_3$(TTHA)]$^{2-}$ The salt from Example 4A (3.00 g, 2.469 mmol) was dissolved in water (24 mL). The pH was adjusted to 6.9 by careful addition of 1M hydrochloric acid. Water was added to 24.60 mL. The osmolality (254 mOsm/Kg) was adjusted to 337 mOsm/Kg by the addition of 73 mg of NaCl. The solution was passed through a 0.22 μM sterile filter and placed in one 30 mL vial. The solution contained 0.10 mmol of the disodium salt of Example 4A per mL. The LD$_{50}$ in mice was found to be greater than 5 mmol/Kg.

EXAMPLE 6

Preparation of the W$_3$($\mu_3$-S)($\mu_2$-S)$_3$ complex of ethylenediamine-N,N,N',N'-tetraacetic acid and diethylenetriamine: W$_3$($\mu_3$-S)($\mu_2$-S)$_3$(EDTA)(dien)

32 mg of EDTA were dissolved in 25 ml of DMF to give a white suspension. 100 mg of W$_3$($\mu_3$-S)($\mu_2$-S)$_3$(H$_2$O)$_9$Cl$_4$ (Intermediate Example 1) were added to the EDTA suspension. The resulting green suspension was refluxed for 30 minutes. 23 mg of dien.nHCl were then slowly added to the refluxing mixture, giving an immediate blue precipitate. The blue suspension was refluxed for 45 minutes to complete the reaction. After cooling the suspension, a grayish purple solid was collected by filtration, washed with ether, then dried in the air. The yield was 0.047 g. MS spectral data showed a molecular ion at 1072, equivalent to the mass of W$_3$($\mu_3$-S)($\mu_2$-S)$_3$(EDTA)(dien)+H.

EXAMPLE 7

Preparation of the dimethylammonium salt of the W$_3$($\mu_3$-S)($\mu_2$-O)$_3$ complex of triethylenetetramine-N,N,N',N,'',N'''-hexaacetic acid: (CH$_3$)$_2$NH$_2$[W$_3$($\mu_3$-S)($\mu_2$-O)$_3$(TTHA)].

0.300 g of W$_3$($\mu_3$-S)($\mu_2$-O)$_3$(H$_2$O)$_9$Cl$_4$ (Intermediate Example 2) were dissolved in 20 mL of DMF, forming a dark orange solution. 0.150 g of TTHA, dissolved in 80 mL of DMF were mixed with the tungsten solution. The mixture was refluxed for 3–4 hours until a pink suspension was obtained. After cooling the suspension, the pink solid was collected by filtration and washed with isopropanol and acetone. The solid material was dried at 50° C. in vacuo. The product was the dimethylammonium salt of $W_3(\mu_3\text{-}S)(\mu_2\text{-}O)_3(\text{TTHA})$. The yield was 0.250 g. UV/VIS absorbances at 280 nm and 480 nm.

Analogous complexes are prepared using:

$W_3(\mu_3\text{-}S)(\mu_2\text{-}S)_2(\mu_2\text{-}O)Cl_4(H_2O)_9$;

$W_3(\mu_3\text{-}S)(\mu_2\text{-}S)(\mu_2\text{-}O)_2Cl_4(H_2O)_9$; and $W_3(\mu_3\text{-}O)(\mu_2\text{-}O)_3Cl_4(H_2O)_9$ (Intermediate Examples 3, 4 and 5).

EXAMPLE 8 Preparation of the $W_3(\mu_3\text{-}S)(\mu_2\text{-}S)_3$ complex of ethylenebis(oxyethylenenitrilo)-tetraacetic acid: $W_3(\mu_3\text{-}S)(\mu_2\text{-}S)_3(\text{EGTA})(H_2O)]$ 440 mg of EGTA were dissolved in 200 ml of DMF to give a colorless solution. 1 g of $W_3(\mu_3\text{-}S)(\mu_2\text{-}S)_3(H_2O)_9Cl_4$; (Intermediate Example 1) was added to the EGTA solution. The resulting dark green solution was refluxed (3–6 hours) until the blue suspension was observed. After cooling the mixture, a grayish purple solid was collected by filtration, washed with ether, and dried in the air. The yield was 0.79 g. $^1$H NMR resonances of this product in $d_6$-DMSO were found at 4.49 ppm (t, 4H), 4.19 ppm (q, 4H, J=15.81 Hz), 3.98 ppm (t, 4H), and 3.60 ppm (s, 4H).

This product was recrystallized in water-methanol-isopropanol mixture and dried in vacuo at 50° C. The analysis indicates that the product is $[W_3(\mu_3\text{-}S)(\mu_2\text{-}S)_3(\text{EGTA})(H_2O)]$.

Analogous complexes are prepared using:

$W_3(\mu_3\text{-}S)(\mu_2\text{-}S)_2(\mu_2\text{-}O)Cl_4(H_2O)_9$;

$W_3(\mu_3\text{-}S)(\mu_2\text{-}S)(\mu_2\text{-}O)_2Cl_4(H_2O)_9$; and $W_3(\mu_3\text{-}O)(\mu_2\text{-}O)_3Cl_4(H_2O)_9$ (Intermediate Examples 3, 4 and 5).

EXAMPLE 9

Preparation of the monosodium salt of the $W_3(\mu_3\text{-}S)(\mu_2\text{-}S)_3$ complex of diethylenetriamine-N,N,N',N'',N''-pentaacetic acid: $Na[W_3(\mu_3\text{-}S)(\mu_2\text{-}S)_3(\text{DTPA})(H_2O)_2]$ 100 mg of $W_3(\mu_3\text{-}S)(\mu_2\text{-}S)_3(H_2O)_9Cl_4$ (Intermediate Example 1) were dissolved in a minimum amount of DMF in a 100 ml round bottom flask, giving a green solution. 38 mg of DTPA were added to the flask. The total volume of DMF was brought up to 25 ml. The mixture was refluxed (2–4 hours) until a grey purple suspension was obtained. After cooling, the grayish purple product was collected by filtration and dried in the air. The yield was 69 mg. The product was obtained as dimethylammonium salt, which was then converted into the sodium salt of $[W_3(\mu_3\text{-}S)(\mu_2\text{-}S)_3(\text{DTPA})(H_2O)_2]$ using the same procedure as shown in Example 4.

Analogous complexes are prepared using:

$W_3(\mu_3\text{-}S)(\mu_2\text{-}S)_2(\mu_2\text{-}O)Cl_4(H_2O)_9$;

$W_3(\mu_3\text{-}S)(\mu_2\text{-}S)(\mu_2\text{-}O)_2Cl_4(H_2O)_9$; and $W_3(\mu_3\text{-}O)(\mu_2\text{-}O)_3Cl_4(H_2O)_9$ (Intermediate Examples 3, 4 and 5).

EXAMPLE 10

Preparation of the disodium salt of the $W_3(\mu_3\text{-}S)(\mu_2\text{-}S)_3$ complex of imino-N,N-diacetic acid: $Na_2[W_3(\mu_3\text{-}S)(\mu_2\text{-}S)_3(\text{IDA})_3]$ 100 mg of $W_3(\mu_3\text{-}S)(\mu_2\text{-}S)_3(H_2O)_9Cl_4$ were dissolved in a minimum amount of DMF in a 100 ml round bottom flask giving a green solution. 42 mg of IDA were added to the flask, followed by DMF. The total volume of DMF was brought up to 25 ml. The mixture was refluxed for 2–4 hours until a blue suspension was observed. After cooling the suspension, the blue product was obtained by filtration and subsequently was dried in the air. The yield was 96 mg.

MS spectral data showed a molecular ion at 1076 equivalent to the mass of $W_3(\mu_3\text{-}S)(\mu_2\text{-}S)_3(\text{IDA})_3+6H$. $^1$H NMR resonances of this product in $D_2O$ were found at 4.11 ppm (q, J=16.3 Hz) and 4.07 ppm (q, J=17.0 Hz). The product was obtained as dimethylammonium salt, which was then converted into the disodium salt of $[W_3(\mu_3\text{-}S)(\mu_2\text{-}S)_3(\text{IDA})_3$ using the same procedure as shown in Example 4.

Analogous complexes are prepared using:

$W_3(\mu_3\text{-}S)(\mu_2\text{-}S)_2(\mu_2\text{-}O)Cl_4(H_2O)_9$;

$W_3(\mu_3\text{-}S)(\mu_2\text{-}S)(\mu_2\text{-}O)_2Cl_4(H_2O)_9$; and $W_3(\mu_3\text{-}O)(\mu_2\text{-}O)_3Cl_4(H_2O)_9$ (Intermediate Examples 3, 4 and 5).

EXAMPLE 11

Preparation of the dimethylammonium salt of the $W_3(\mu_3\text{-}S)(\mu_2\text{-}S)_3S$ complex of N',N'-di[bis(hydroxyethyl)aminoethyl]-N,N,N''',N'''-tetraacetic acid triethylenetetramine: $(CH_3)_2NH_2[W_3(\mu_3\text{-}S)(\mu_2\text{-}S)_3(\text{TTBA-BDHA})]$ 175 mg ($2.62\times10^{-4}$ moles) of TTHA-BDHA were dissolved in 25 mL of DMF. 250 mg ($2.39\times10^{-4}$ moles) of $W_3(\mu_3\text{-}S)(\mu_2\text{-}S)_3(H_2O)_9Cl_4$ were added to the solution. The resulting dark green solution was refluxed (2–4 hours) until a black suspension was observed. After cooling the suspension, the black solid was collected by filtration and washed with isopropanol and acetone. The solid material was dried at 50° C. in vacuo. The product was the dimethylammonium salt of $[W_3(\mu_3\text{-}S)(\mu_2\text{-}S)_3(\text{TTHA-BDHA})]$. The yield was 350 mg. UV/vis spectroscopy shows $\lambda_{max}$ at 310 nm and 570 nm.

EXAMPLE 12

Preparation of the tetrasodium salt of $(W_2O_2(\mu_2\text{-}O)_2)_2^{4+}$ complex of 1,2,4,5 Benzenetetra(iminodiacetate): $Na_4[(W_2O_2(\mu_2\text{-}O)_2)_2(\text{BTIDA})]$ a) Synthesis of 1,2,4,5-Benzenetetra(iminodi-t-butylacetate)

One equivalent of 1,2,4,5-benzenetetramine tetrahydrochloride is dissolved in chloroform with 10 equivalents diisopropylethylamine. To this solution is added 10 equivalents bromo-t-butyl acetate dropwise with stirring. The resulting solution is heated to 50° C. for 48 hours. The solution is then washed three times with water, dried over $MgSO_4$, and the solvent evaporated in vaco.

b) Synthesis of 1,2,4,5 Benzenetetra(iminodiacetate) [BTIDA]

1,2,4,5-Benzenetetra(iminodi-t-butylacetate) is dissolved in methylene chloride and trifluoroacetic acid is added dropwise. The solution is stirred for one hour, and the hydrolysis is repeated three times to give 1,2,4,5 Benzenetetra(iminodiacetate), which is then purified by chromatography on AG1-X8 ion-exchange resin.

c) Synthesis of the title compound 0.5 g of 1,2,4,5 Benzenetetra (iminodiacetate), BTIDA, and 1 g of sodium acetate is dissolved in 35 mL of hot water. 1 g of $Na_3[WO_2(C_2O_4)_2]\cdot3H_2O$ (prepared according to Soares et al. J.C.S. Dalton, 1101–1104 (1980)), are directly added to the BTIDA solution. The resulting solution is boiled on a hot plate for 10 minutes to complete the substitution reaction of the coordinated oxalate with BTIDA. 2 g of $CaCl_2.2H_2O$ solution in 10 ml of hot water is then added to the orange tungsten solution to precipitate $CaC_2O_4$. After removing the white $CaC_2O_4$ solid by filtration, the orange filtrate is treated with 1.5 g of $BaCl_2.2H_2O$ to obtain $Ba[W_2O_2(\mu_2-O_2)_2(BTIDA)]$.

The resulting orange solution is concentrated to 25 ml under reduced pressure to precipitate the excess salts. After the salt is removed by filtration, the orange filtrate is placed on a sephadex G-15 column. The orange eluant with water is treated with $Na_2SO_4$ to convert the barium complex into the sodium one. The insoluble $BaSO_4$ is filtered off and the orange filtrate is reduced to a small volume, 15 ml. The concentrated orange filtrate is mixed with ethanol to precipitate the title product. The orange precipitate is collected by filtration, washed with acetone, and dried in the air.

EXAMPLE 13

Preparation of
$[Na_2][(WO_2)_2(\mu\text{-oxo})\text{-bis}(\mu\text{-hydroxo})\text{mannitol}]$:
$[Na_2W_2O_5(_6H_{10}O_6)]$ This procedure is modified from Llopis et al. Polyhedron 5: 2069–2074 (1986). Ten grams of sodium tungstate dihydrate (0.03 mole) and 2.76 g of D-mannitol (0.015 mole) were dissolved in 25 mL of deionized water with stirring. Concentrated hydrochloric acid (2.53 mL, 0.03 mole) was then added dropwise (pH should not fall below 6). A white-yellow precipitate formed on acid addition. The solution was heated and stirred until the precipitate dissolved leaving a clear, homogeneous solution. Acetone (150 mL) was then added and a clear oil separated. The solution was decanted from the oil and fresh acetone was added causing the oil to begin to solidify. After decanting, fresh acetone was added for a third time finally converting the original oil to an immobile white paste. Absolute ethanol (150 mL) was added to the paste and the mixture heated to boiling. During heating, the paste was triturated to a fine, free-flowing solid. The solid was collected, washed with absolute ethanol, and dried under vacuum at 40° C., to give the title compound. Yield was 10.2 g (99%). FAB+ mass spectroscopy showed two parent ions: (M+H)+ at 672.9 (calculated value is 672.8) and (M+Na)+ at 694.9 (calculated value is 694.8).

EXAMPLE 14

Preparation of the $W_4(\mu_{23}\text{-S})_4$ complex of pyridine:
$[W_4(\mu_3\text{-S})_4(py)_19 Cl_n$ (n=4, 5, or 6)

The title compound was prepared by refluxing the mixture of $W_3(\mu_3\text{-S})(\mu_2\text{-S})_3(H_2O)_9Cl_4$ (Intermediate Example 1) and $W(CO)_6$ in pyridine. 50 mg of $W_3(\mu_3\text{-S})(\mu_2\text{-S})_3(H_2O)_9Cl_4$ were dissolved in 3 mL of $N_2$ saturated pyridine giving a dark green solution, followed by the addition of 20 mg of $W(CO)_6$. The resulting green suspension was refluxed under $N_2$ for an hour. During the reflux, the $W(CO)_6$ was dissolved into the green solution, which eventually became a brown suspension. The brown suspension was mixed with 2–3 ml of ether to precipitate more product. Greenish yellow solid was collected by filtration, washed with ether, and dried in the air. The yield was 80 mg. MS spectral data showed a parent ion at 1180, corresponding to the mass of $W_4S_4(py)_4$+ H. Other fragment ions at 1099, 1023, 944, and 865 were also observed, equal to the masses of $W_4S_4(py)_3$+2H, $W_4S_4(py)_2$+2H, $W_4S_4(py)$+H, and $W_4S_4$+H, respectively.

EXAMPLE 15

Preparation of the Tris(pyrazolyl)hydridoborate complex of $W_2O_2(\mu_2\text{-O})_2$: $(HB(PZ)_3)_2W_2O_2(\mu_2\text{-O})_2$ The salt, $Na_3[WO_2(C_2O_4)_2].3H_2O$ (1 g, 2 mmoles; prepared by method of J.C.S. Dalton (1980) 1101–1104), is added to 50 mL of distilled water containing $Na[HB(PZ)_3]$ (0.96 g, 4 mmole; PZ=pyrazole; prepared by the method of JACS 89: 3170, 3904, 6288 (1967). The resulting solution is heated to about 80° C. for about 0.5 hours to complete coordination of the pyrazolylborate ligand. Purification by column chromatography (Sephadex G-15) is used to isolate the title compound.

EXAMPLE 16

Preparation of $K_2[SiW_{11}O_{40}(Si(CH_2)_3N(CH_3)_3)_2]^0$

The salt, $K_8SiW_{11}O_{39}$ (4 g, 0.125 mmole; prepared by the method of Inorg. Chem. 16; 2115 (1977) is dissolved in 100 mL distilled water. N-trimethoxysilylpropyl-N,N,N-trimethylammonium chloride (51 mL of a 50% MeOH solution, about 10 mmol) is added with vigorous stirring. Solution pH is adjusted to 1 with 1N HCl. A white solid is removed by filtration and the title salt is isolated by crystallization.

EXAMPLE 17

$[[CH_3(CH_2)_3]_4N]_3PW_{12}O_{40}$ 1.00 g ($3.46\times10^{-4}$ moles) of 12-phosphotungstic acid ($H_3PW_{12}O_{40}$, Johnson Matthey) was dissolved in a minimum of deionized water and 0.364 g ($1.13\times10^{-3}$ moles) of tetrabutylammonium bromide ($[CH_3(CH_2)_3]_4NBr$, Aldrich) was dissolved in 10 mL of deionized water. The two solutions were mixed and allowed to stand at 25° C. for one hour, during which time a white precipitate formed. The solid was isolated and recrystallized from a minimum volume of hot $CH_3CN$. About 800 mg of a white solid was collected by filtration.

EXAMPLE 18

$[[CH_3(CH_2)_3]_4N]_4SiW_{12}O_{40}$ 1.00 g ($3.46\times10^{-4}$ moles) of 12-tungstosilicic acid ($H_3SiW_{12}O_{40}$, Electron Microscopy Services) was dissolved in a minimum of deionized water and 0.476 g ($1.47\times10^{-3}$ moles) of tetrabutylammonium bromide ($[CH_3(CH_2)_3]_4NBr$, Aldrich) was dissolved in 10 mL of deionized water. The two solutions were mixed and allowed to stand at 25° C. for one hour, during which time a white precipitate formed. The solid was isolated and recrystallized from a minimum volume of hot $CH_3CN$. A white solid was collected by filtration.

EXAMPLE 19

Preparation of $[CH_3(CH_2)_{11}N(CH_3)_3PW_{12}O_{40}$ 1.00 g ($3.47\times10^{-4}$ moles) of 12-phosphotungstic acid ($H_3PW_{12}O_{40}$, Johnson Matthey) was dissolved in a minimum volume of deionized water and 0.348 g ($1.13\times10^{-3}$ moles) of dodecyltrimethylammonium bromide ($CH_3(CH_2)_{11}N(CH_3)_3Br$, Aldrich) was dissolved in 10 mL of deionized water. The two solutions were mixed and allowed to stand at 25° C. for one hour during which time a white precipitate formed. The solid was isolated and recrystallized from a minimum volume of hot $CH_3CN$ and collected by filtration. Yield was about 200 mg.

EXAMPLE 20

Preparation of $[CH_3(CH_2)_{11}N(CH_3)_3]_4SiW_{12}O_{40}$ 1.00 g ($3.47 \times 10^{-4}$ moles of 12-tungstosilicic acid ($H_3SiW_{12}O_{40}$, Electron Microscopy Services) was dissolved in a minimum of deionized water and 0.453 g ($1.47 \times 10^{-3}$ moles) of dodecyltrimethylammonium bromide ($CH_3(CH_2)_{11}N(CH_3)_3Br$, Aldrich) was dissolved in 10 mL of deionized water. The two solutions were mixed and allowed to stand at 25° C. for one hour, during which time a yellow white precipitate formed. The solid was isolated and recrystallized from a minimum volume of hot $CH_3CN$ and collected by filtration. Yield was about 200 mg.

EXAMPLE 21

Preparation of $[C_{12}\text{-py}]_3PW_{12}O_{40}$ 1.00 g ($3.47 \times 10^{-4}$ moles) of 12-phosphotungstic acid ($H_3PW_{12}O_{40}$, Johnson Matthey) was dissolved in a minimum volume of deionized water and 0.341 g ($1.13 \times 10^{-3}$ moles) of dodecylpyridinium chloride ($C_{12}$-pyCl, Aldrich) was dissolved in 10 mL of deionized water. The two solutions were mixed and allowed to stand at 25° C. for one hour, during which time a white precipitate formed. The solid was isolated and recrystallized from a minimum volume of hot $CH_3CN$ and collected by filtration. Yield was about 200 mg.

EXAMPLE 22

Preparation of $(C_{12}\text{-py})_4SiW_{12}O_{40}$ 1.00 g ($3.47 \times 10^{-4}$ moles) of 12-tungstosilicic acid ($H_3SiW_{12}O_{40}$, Electron Microscopy Services) was dissolved in a minimum of deionized water and 0.443 g ($1.47 \times 10^{-3}$ moles) of dodecylpyridinium chloride ($C_{12}$-pyCl, Aldrich) was dissolved in 10 mL of deionized water. The two solutions were mixed and allowed to stand at 25° C. for one hour, during which time a yellow white precipitate formed. The solid was isolated and recrystallized from a minimum volume of hot $CH_3CN$ and collected by filtration. Yield was about 800 mg.

EXAMPLE 23

Preparation of $[CH_3(CH_2)_{15}N(CH_3)_3]_3PW_{12}O_{40}$ 1.00 g ($3.47 \times 10$moles) of 12-phosphotungstic acid ($H_3PW_{12}O_{40}$, Johnson Matthey) was dissolved in a minimum volume of deionized water and 0.632 g ($1.13 \times 10^{-3}$ moles) of cetyltrimethylammonium bromide ($CH_3(CH_2)_{15}N(CH_3)_3Br$, Aldrich) was dissolved in 10 mL of deionized water. The two solutions were mixed and allowed to stand at 25° C. for one hour, during which time a white precipitate formed. The solid was isolated and recrystallized from a minimum volume of hot $CH_3CN$ and collected by filtration. Yield was about 600 mg.

EXAMPLE 24

Preparation of $[CH_3(CH_2)_{15}N(CH_3)_3]_4SiW_{12}O_{40}$ 1.00 g ($3.47 \times 10^{-4}$ moles) of 12-tungstosilicic acid ($H_3SiW_{12}O_{40}$, Electron Microscopy Services) was dissolved in a minimum of deionized water and 0.842 g ($2.31 \times 10^{-3}$ moles) of cetyltrimethylammonium bromide ($CH_3(CH_2)_{15}N(CH_3)_3Br$, Aldrich) was dissolved in 10 mL of deionized water. The two solutions were mixed and allowed to stand at 25° C. for one hour, during which time a yellow white precipitate formed. The solid was isolated and recrystallized from a minimum volume of hot $CH_3CN$ and collected by filtration. Yield was about 800 mg.

EXAMPLE 25

Preparation of $[(C_{16}\text{-py}]_3PW_{12}O_{40}$ 1.00 g ($3.47 \times 10^{-4}$ moles) of 12-phosphotungstic acid ($H_3PW_{12}O_{40}$, Johnson Matthey) was dissolved in a minimum volume of deionized water and 0.698 g ($1.73 \times 10^{-3}$ moles) of 1-hexadecylpyridinium chloride ($C_6$-pyCl, Aldrich) was dissolved in 10 mL of deionized water. The two solutions were mixed and allowed to stand at 25° C. for one hour, during which time a white precipitate formed. The solid was isolated and recrystallized from a minimum volume of hot $CH_3CN$ and collected by filtration. Yield was about 600 mg.

EXAMPLE 26

Preparation of $[(C_{16}\text{-py}]_4SiW_{12}O_{40}$ 1.00 g ($3.47 \times 10$moles) of 12-tungstosilicic acid ($H_3SiW_{12}O_{40}$, Electron Microscopy Services) was dissolved in a minimum of deionized water and 0.929 g ($2.31 \times 10^{-3}$ moles) of 1-hexadecylpyridinium chloride ($C_{16}$-pyCl, Aldrich) was dissolved in 10 mL of deionized water. The two solutions were mixed and allowed to stand at 25° C. for one hour, during which time a yellow white precipitate formed. The solid was isolated and recrystallized from a minimum volume of hot $CH_3CN$ and collected by filtration. Yield was about 700 mg.

EXAMPLE 27

Preparation of a ferromagnetically coupled hexanuclear ferric complex with an S=5 ground state 3.1 equivalents of the chelating ligand 1.1-bis(N-methylimidazol-2-yl)ethanol (1) is reacted with the acetato-oxo $Fe_3$(III)-complex $[Fe_3O(OAc)_6(py)_6]ClO_4$ (2) to give a brown solution of a hexanuclear Fe(III) complex. After 20 minutes the solution is concentrated in vacuo and a brown oil is obtained. Addition of $CH_2Cl_2$ to the brown oil gives a brown solution, which is kept in an open flask at ambient temperature. Upon slow evaporation of solvent, red block-like crystals of the title compound (3) as a $CH_2Cl_2$ solvate containing 8 equivalents of $CH_2Cl_2$ suitable for characterisation by X-ray crystallography can be obtained. Further drying gives (3) as a monomethylene chloride solvate in 40% yield.

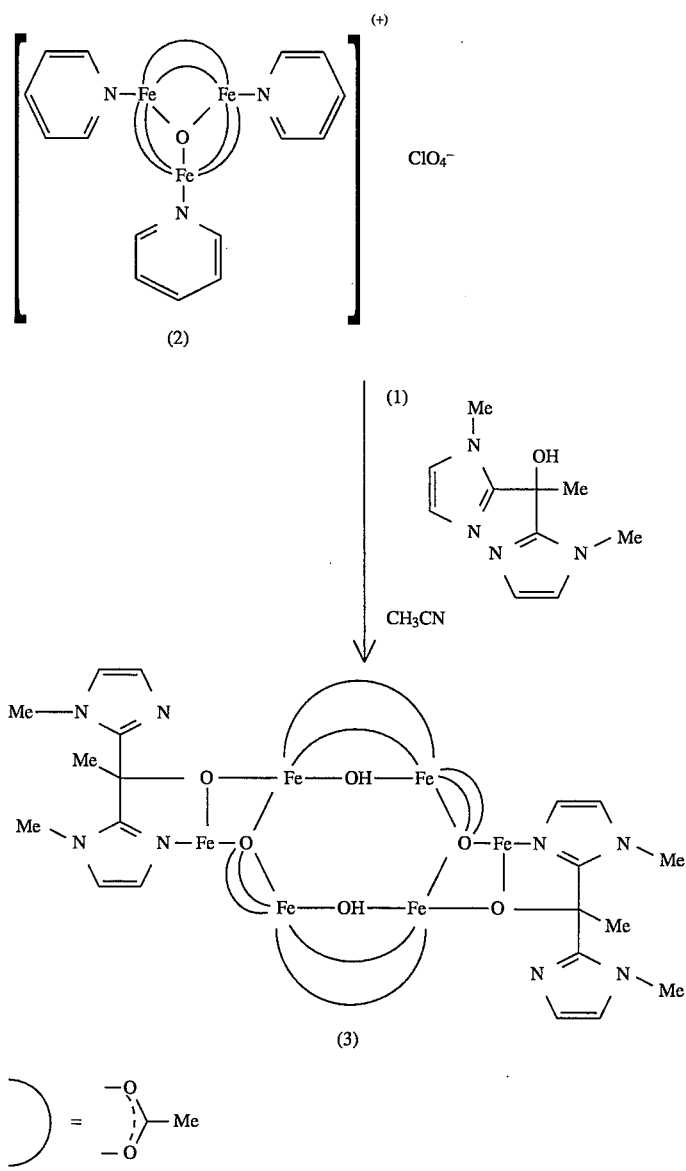

EXAMPLE 28

Preparation of Ln₃Cu complexes where Ln=Gd, Dy

These complexes can be synthesized by using two different procedures. At first, equimolar amounts of Ln(hfac)$_3$.H$_2$O and CuSALtn are mixed in CHCl$_3$. Two different kinds of crystals: green crystals corresponding to the Ln(hfac)$_3$CuSatn adducts and a small amount of light blue crystals of formula Ln(hfac)$_3$CuSatnOH(CuSatnOH= [N-(3-aminopropyl)-salicylaldiminato]hydroxocopper(II)) can be obtained.

These derivatives are the products of the partial hydrolysis of the copper (II) coordinate Schiff base ligand.

An alternative synthesis starts with the preparation of the CuSatnOH ligand. A 20-mmol sample of Cu(CH$_3$COO)$_2$.H$_2$O is dissolved in 100 mL of a 50% ethanol-water solution; then 20 mmol of salicylaldehyde and 2.5 mmol of NaOH are added, and the solution is heated under stirring. After 5 min, 20 mmol of 1.3-diaminopropane is added and the solution is reduced to 50 mL. After cooling, a dark green precipitate is collected and it analyses well for CuSatnOH.

From an equimolar solution of Ln(hfac)$_3$ and CuSatnOH in pure chloroform, only light blue crystals are obtained, which analyse satisfactorily for Ln(hfac)$_3$CuSatnOH.

EXAMPLE 29

Diagnostic Compositions

Formation of Compounds into Diagnostic Compositions:

Compounds such as [[CH$_3$(CH$_2$)$_3$]$_4$N]$_3$PW$_{12}$O$_{40}$, [[CH$_3$(CH$_2$)$_3$N]$_4$SiW$_{12}$O$_{40}$, [CH$_3$(CH$_2$)$_{11}$N(CH$_3$)$_3$]$_3$PW$_{12}$O$_{40}$, [CH$_3$(CH$_2$)$_{11}$N(CH$_3$)$_3$]$_4$SiW$_{12}$O$_{40}$, [(C$_{12}$-py)]$_3$PW$_{12}$O$_{40}$, [(C$_{12}$-py)]$_4$SiW$_{12}$O$_{40}$, [CH$_3$(CH$_2$)$_{15}$N(CH$_3$)$_3$]$_3$PW$_{12}$O$_{40}$, [CH$_3$(CH$_2$)$_{15}$N(CH$_3$)$_3$]$_4$SiW$_{12}$O$_{40}$, [(C$_{16}$-py)]$_3$PW$_{12}$O$_{40}$, [(C$_{16}$-py)]$_4$SiW$_{12}$O$_{40}$, and others described in the foregoing Examples which are soluble in organic solvents can be made into emulsions to prepare oral diagnostic CM using edible oils. A list of these oils and other important emulsifying agents appears below:

Cetomacrogal Emulsifying Wax: A non-ionic emulsifying agent which contains cetostearyl alcohol and cetomacrogol; considered non-toxic; forms a pourable product using 5% wax; recommended for use with salts of polyvalent metals and medicaments based on nitrogenous compounds. Reference: *J. Pharm Pharmacol.*, 6:816 (1954).

Cetyl Alhohol: $CH_3(CH_2)_{14}CH_2OH$; used as an emulsifier in 2–5% concentrations; commonly used for suppositories.

Cholesterol: $C_{27}H_{46}O$; can be used as an emulsifying agent; some reported complicity of cholesterol in atherosclerosis and gallstones; Reference: *J. Pharm Sci.*, 71(3) 370 (1982); *J. Pharm Sci.*, 71(2) 182 (1982).

Corn oil: Composed of 44% oleic acid; 39% linoleic acid; 7% palmitic acid; 3% stearic acid, and other components; used as an oral nutritional supplement 67% as an emulsion; no toxicity from oral ingestion reported.

Cottonseed oil: Composed of 39% linoleic acid; 33% oleic acid; 19% palmitic acid; 2% stearic acid, and other components; used as an IV emulsifying agent in 10–15% w/v concentration; some side effects of IV use reported; Reference: *J. Am. Med. Assoc.*, 166, 1042 (1958).

Diethanolamine: $(HOCH_2CH_2)_2NH$; $LD_{50}$ for oral ingestion=1.5 g/kg; reported to be used via salt formation to solubilize iodinated organic acids used as contrast media.

Glycerol monostearate: $C_{20}H_{40}O_4$; non-toxic and edible; used as an emulsifying aid; useful with quat salts; Reference: *Am. Prof. Pharmacy*, 16,874 (1950); *Am. J Hosp. Pharm.*, 24,143 (1967).

Sesame seed oil: Composed of 45% oleic acid; 40% linoleic acid; 9% palmitic acid; 4% stearic acid, and other components; acute oral $LD_{50}$=>15 g/kg; Reference: *J. Pharm Sci.*, 71(5) 495 (1982).

Emulsion stabilizers: Bentonite; Calcium Stearate; Carnauba Wax; Dextrin; Glycerol monostearate; Hydroxyroyl cellulose; Hydroxyroyl methylcellulose; Magnesium aluminum silicate; mineral oil; lanolin oil; polacrilin potassium; propylene glycol; poloxamer.

We claim:

1. A sterile X-ray contrast medium comprising a physiologically tolerable multinuclear complex of formula I $$(M_nB_uA_v)_xL_w \qquad (I)$$

(where $M_nB_uA_v$ is a multinuclear entity; each M which may be the same or different is a contrast enhancing metal atom covalently bonded to at least one atom B where u is non-zero; each B which may be the same or different is a non-metal bridging atom covalently bonded to at least two metal atoms M and optionally to further atoms; each A which may be the same or different is a non-metal non-bridging atom covalently bonded to a metal atom M; each L which may be the same or different is a ligand co-ordinately bonded to at least one metal atom M; n is a positive integer of value 2 or greater at least one metal atom M being tungsten or a lanthanide where n represents 2; u is zero or a positive integer, u being at least 2 unless n is at least 5 or at least one M is a lanthanide; x is a positive integer; and v and w are independently zero or positive integers; with the provisos that where n is 2 or 3 and no M is a lanthanide either at least one B is other than oxygen or sulphur or w is a positive integer and at least one L is a multidentate ligand other than EDTA) or a physiologically tolerable salt thereof, together with at least one pharmaceutical carrier or excipient.

2. A medium as claimed in claim 1 wherein n represents a positive integer of value 3 or greater.

3. A medium as claimed in claim 1 wherein n represents a positive integer of either 2 or 3 and L is selected from PDTA, EDT, TTHA, dien, EGTA, IDA and HB (PX).

4. A medium as claimed in claim 1 wherein n represents a positive integer of value 4.

5. A medium as claimed in claim 1, wherein n represents a positive integer of value 6 to 100.

6. A medium as claimed in claim 1 wherein n represents a positive integer of value 4, 6, 11, 12 or 18.

7. A medium as claimed in claim 1 wherein n represents a positive integer of value 4, 6, 11, 12 or 18.

8. A medium as claimed in claim 1 wherein n is 2 or 3 and at least one B represents other than oxygen or sulphur.

9. A medium as claimed in to claim 1 wherein in formula I at least one M is selected from W, Mo, Re, Rh, Tc, V, Nb, Ta, Ru, Gd, Dy, Mn and Fe.

10. A medium as claimed in claim 1 wherein at least one B is selected from O, S, Se, Te, Cl, Br, I, N and P.

11. A medium as claimed in claim 1 wherein n represents a positive integer having a value of up to 30 and u represent an integer of value 2 to 30.

12. A medium as claimed in claim 1 wherein said complex is a polyoxide containing 12 to 200 oxygen or oxygen-containing bridging groups.

13. A medium as claimed in claim 10 wherein w is at least 1 and at least one L is an optionally substituted polyamine, polyalcohol, polyether or polyacid.

14. A medium as claimed in claim 13 wherein at least one L is a linear, branched or cyclic polyamino-polycarboxylic acid.

15. A medium as claimed in claim 14 wherein L is of formula $$(R^2)_2NCH_2CH_2\underset{R^1}{N}CH_2CH_2\underset{R^1}{N}CH_2CH_2N(R^2)_2$$

where $R^1$ which may be the same or different represent $R^2$, $C_{1-4}$hydroxyalkyl, carboxy-$C_{1-4}$alkyl or amino-$C_{1-4}$alkyl groups or together both $R^1$ groups represent a group $CH_2CH_2NR^3CH_2CH_2$ where $R^3$ is an $R^2$ group or a $C_{1-4}$ alkyl group optionally substituted by hydroxyl, carboxyl, aryl or amino groups, each $R^2$ independently represents a hydrogen atom or an optionally amidated or esterified carboxy $C_{1-4}$ alkyl group, wherein any amine nitrogen is substituted by group selected from hydrogen atoms and optionally hydroxylated $C_{1-4}$ alkyl groups.

16. A medium as claimed in claim 13 wherein L is selected from $(HOOCCH_2)_2NCH_2CH_2N(CH_2CH_2OH)CH_2CH_2N(CH_2CH_2OH)CH_2CH_2N(CH_2COOH)_2$
$(HOCH_2CH_2)_2NCOCH_2N(CH_2COOH)CH_2CH_2(N(CH_2COOH)CH_2CH_2)_2N(CH_2COOH)CH_2CON(CH_2CH_2OH)_2$
$(HOOCCH_2)_2NCH_2CH(CH_3)N(CH_2COOH)_2$
$H_2NCH_2CH_2N(CH_2COOH)CH_2CH_2N(CH_2COOH)CH_2CH_2NH_2$ -continued (HOOCCH$_2$)$_2$NCH$_2$CH$_2$N(CH$_2$CH$_2$N(CH$_2$CH$_2$OH)$_2$)CH$_2$CH$_2$N(CH$_2$CH$_2$N(CH$_2$CH$_2$OH)$_2$)CH$_2$CH$_2$N(CH$_2$COOH)$_2$
(HOOCCH$_2$)$_2$NCH$_2$CH$_2$N(CH$_2$COOH)CH$_2$CH$_2$N(CH$_2$COOH)CH$_2$CH$_2$N(CH$_2$COOH)$_2$
and

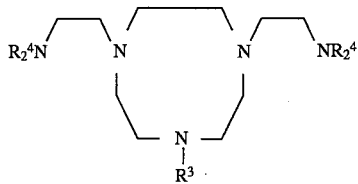

where each R$^4$ is hydrogen or carboxymethyl and R$^3$ is hydroxyalkyl or N-carboxymethylated amino alkyl.

17. A medium as claimed in claim 1 wherein w is at least 1 and at least one L is an optionally substituted pyrazole.

18. A medium as claimed in claim 17 wherein at least one L is a trispyrazolylborate.

19. A medium as claimed in claim 1 wherein at least one L is a polychelant.

20. A medium as claimed in claim 1 wherein n is an integer having the value 3 to 6, u is an integer having the value 4 to 8, at least one M is selected from W and Mo and at least one B is selected from O, S, Se and Te.

21. A medium as claimed in claim 1 wherein the multinuclear entity comprises a unit of formula M$_3$(M$_3$B) ($\mu_2$B)

M$_4$($\mu_3$B)$_4$ or

M$_4$($\mu_2$B)$_3$ where each M is independently Mo or W, and each B is independently O, S, Se or Te or a nitrogen or phosphorus atom covalently bonded to a proton or an organic group, with the proviso for M$_3$($\mu_3$B) ($\mu_3$B)$_3$ that at least one B represents other than oxygen or sulphur.

22. A medium as claimed in claim 1 comprising a contrast agent selected from the chelate complexes of W$_4$S$_4$, W$_{12}$O$_{40}$ and W$_{18}$O$_{62}$.

23. A medium as claimed in claim 21 comprising a contrast agent selected from the EDTA, TTHA, DTPA, IDA, and EGTA chelate complexes of W$_3$S$_4$.

24. A medium as claimed in claim 1 comprising a multinuclear entity of formula W$_a$S$_b$O$_c$ where a is 3, b is 1, 2, 3 or 4, c is 0, 1, 2 or 3 and b+c is 4.

25. A medium as claimed in claim 1 comprising a multinuclear entitity of formula W$_a$S$_b$O$_c$ where a is 4, b is 1, 2, 3 or 4, c is 0, 1, 2 or 3 and b+c is 4.

26. A method of generating an X-ray image of a human or animal body which method comprises administering to said body a contrast medium as claimed in any one of claims 1 to 21 and generating an X-ray image of at least a part of said body into which sad medium distributes.

27. A compound as claimed in claim 1 wherein L is selected from TTHA-BDHA; N',N''-di[bis(hydroxyethyl)aminoethyl] N,N,N''',N'''-tetraacetic acid-triethylenetetramine; N,N'-di[bis(carboxymethyl)aminoethyl]N''-hydroxyethyl-TACN; tris[(dicarboxymethyl)aminoethyl]TACN; tris[dicarboxymethyl)aminoethyl]TACN; N',N''-bis(carboxymethyl)triethylene tetramine; N,N',N''',N'''-tetra(carboxymethyl)-N',N''-bis(hydroxyethyl) triethylene tetramine; and the salts and chelate complexes thereof.

* * * * *